(12) United States Patent
Aftab et al.

(10) Patent No.: US 10,273,211 B2
(45) Date of Patent: Apr. 30, 2019

(54) METABOLITES OF N-{4-([6,7-BIS(METHYLOXY) QUINOLIN-4-YL]OXY}PHENYL)-N'-(4-FLUOROPHENYL)-CYCLOPROPANE-1,1-DICARBOXAMIDE

(71) Applicant: Exelixis, Inc., South San Francisco, CA (US)

(72) Inventors: Dana T. Aftab, San Rafael, CA (US); Sriram Naganathan, San Jose, CA (US); Wei Xu, Danville, CA (US); Steven Lacy, San Mateo, CA (US); Linh Nguyen, San Francisco, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 14/776,337

(22) PCT Filed: Mar. 17, 2014

(86) PCT No.: PCT/US2014/030524
§ 371 (c)(1),
(2) Date: Sep. 14, 2015

(87) PCT Pub. No.: WO2014/145715
PCT Pub. Date: Sep. 18, 2014

(65) Prior Publication Data
US 2016/0031818 A1 Feb. 4, 2016

Related U.S. Application Data

(60) Provisional application No. 61/792,413, filed on Mar. 15, 2013.

(51) Int. Cl.
| | |
|---|---|
| C07D 215/22 | (2006.01) |
| C07C 305/24 | (2006.01) |
| C07C 233/60 | (2006.01) |
| C07D 215/60 | (2006.01) |
| G01N 33/487 | (2006.01) |

(52) U.S. Cl.
CPC .......... C07D 215/22 (2013.01); C07C 233/60 (2013.01); C07C 305/24 (2013.01); C07D 215/60 (2013.01); G01N 33/487 (2013.01); *C07C 2601/02* (2017.05); *G01N 2570/00* (2013.01)

(58) Field of Classification Search
None
See application file for complete search history.

(56) References Cited

U.S. PATENT DOCUMENTS

| | | | |
|---|---|---|---|
| 7,579,473 B2 | 8/2009 | Bannen et al. | |
| 7,977,345 B2 | 7/2011 | Bannen et al. | |
| 7,999,006 B2 | 8/2011 | Lamb | |
| 8,067,436 B2 | 11/2011 | Bannen et al. | |
| 8,178,532 B2 | 5/2012 | Bannen et al. | |
| 8,314,232 B2 | 11/2012 | Deschamps et al. | |
| 8,476,298 B2 | 7/2013 | Bannen et al. | |
| 8,497,284 B2 | 7/2013 | Bannen et al. | |
| 8,673,912 B2 | 3/2014 | Cannon et al. | |
| 8,877,776 B2 | 11/2014 | Brown et al. | |
| 8,933,230 B2 | 1/2015 | Yun et al. | |
| 9,174,947 B2 | 11/2015 | Bannen et al. | |
| 9,365,516 B2 | 6/2016 | Wilson et al. | |
| 9,717,720 B2 | 8/2017 | Wilson et al. | |
| 9,724,342 B2 | 8/2017 | Wilson et al. | |
| 9,809,549 B2 | 11/2017 | Brown et al. | |
| 9,861,624 B2 | 1/2018 | Aftab et al. | |
| 9,969,692 B2 | 5/2018 | Wilson et al. | |
| 10,034,873 B2 | 7/2018 | Wilson et al. | |
| 10,039,757 B2 | 9/2018 | Wilson et al. | |
| 2008/0161305 A1 | 7/2008 | Forsyth et al. | |
| 2009/0274693 A1 | 11/2009 | Gilmer et al. | |
| 2011/0077233 A1 | 3/2011 | Bannen et al. | |
| 2012/0070368 A1 | 3/2012 | Bannen et al. | |
| 2012/0184523 A1 | 7/2012 | Bannen et al. | |
| 2012/0252840 A1 | 10/2012 | Aftab et al. | |
| 2012/0282179 A1 | 11/2012 | Aftab et al. | |
| 2013/0030172 A1 | 1/2013 | Wilson et al. | |
| 2013/0142790 A1 | 6/2013 | Gilmer et al. | |
| 2013/0143881 A1 | 6/2013 | Cannon et al. | |
| 2013/0150363 A1 | 6/2013 | Gilmer et al. | |
| 2013/0197230 A1 | 8/2013 | Wilson et al. | |
| 2013/0252940 A1 | 9/2013 | Bannen et al. | |
| 2013/0252956 A1 | 9/2013 | Kallender et al. | |
| 2013/0330377 A1 | 12/2013 | Wilson | |
| 2013/0337015 A1 | 12/2013 | Wilson | |
| 2014/0057908 A1 | 2/2014 | Smith et al. | |
| 2014/0057943 A1 | 2/2014 | Smith et al. | |
| 2014/0066444 A1 | 3/2014 | Smith et al. | |

(Continued)

FOREIGN PATENT DOCUMENTS

| | | |
|---|---|---|
| CN | 103664776 | 5/2016 |
| WO | 2005030140 | 4/2005 |

(Continued)

OTHER PUBLICATIONS

Business Wire Bulletin Oct. 1, 2011, accessed online at www.euroinvestor.com on Nov. 30, 2016.*

(Continued)

*Primary Examiner* — Heidi Reese
(74) *Attorney, Agent, or Firm* — Honigman LLP; Heidi M. Berven; Jonathan P. O'Brien

(57) ABSTRACT

The invention relates to metabolites of cabozantinib (I) as well as uses thereof.

(I)

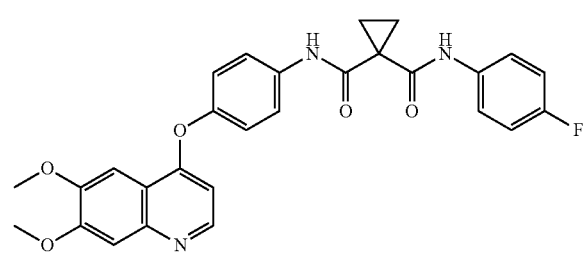

2 Claims, No Drawings

(56) References Cited

U.S. PATENT DOCUMENTS

| | | |
|---|---|---|
| 2014/0121239 A1 | 5/2014 | Aftab |
| 2014/0155396 A1 | 6/2014 | Bannen et al. |
| 2014/0179736 A1 | 6/2014 | Schwab et al. |
| 2014/0200242 A1 | 7/2014 | Wilson |
| 2014/0221372 A1 | 8/2014 | Kulkarni et al. |
| 2014/0228401 A1 | 8/2014 | Aftab et al. |
| 2014/0302012 A1 | 10/2014 | DeCillis et al. |
| 2014/0323522 A1 | 10/2014 | Aftab et al. |
| 2015/0057310 A1 | 2/2015 | Brown et al. |
| 2015/0133494 A1 | 5/2015 | Aftab |
| 2015/0196545 A1 | 7/2015 | Aftab et al. |
| 2015/0202196 A1 | 7/2015 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0022662 A1 | 1/2016 | DeCillis |
| 2016/0031818 A1 | 2/2016 | Aftab et al. |
| 2016/0051532 A1 | 2/2016 | Aftab et al. |
| 2016/0082019 A1 | 3/2016 | Sweeney et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0044106 A1 | 2/2017 | Aftab et al. |
| 2017/0057921 A1 | 3/2017 | Wilson et al. |
| 2017/0087143 A1 | 3/2017 | Aftab et al. |
| 2017/0143689 A1 | 5/2017 | Wilson et al. |
| 2017/0266178 A1 | 9/2017 | Wilson et al. |
| 2017/0275251 A1 | 9/2017 | Brown et al. |
| 2017/0355678 A1 | 12/2017 | Bannen et al. |
| 2018/0002289 A1 | 1/2018 | Brown et al. |
| 2018/0037552 A1 | 2/2018 | Brown et al. |
| 2018/0230100 A1 | 8/2018 | Wilson et al. |

FOREIGN PATENT DOCUMENTS

| | | | |
|---|---|---|---|
| WO | WO 2005030140 A2 * | 4/2005 | ............. A61K 31/47 |
| WO | 2007099326 | 9/2007 | |
| WO | 2012088337 | 6/2012 | |
| WO | 2014039971 | 3/2014 | |
| WO | 2014145693 | 9/2014 | |
| WO | 2015142928 | 9/2015 | |
| WO | 2016019285 | 2/2016 | |

OTHER PUBLICATIONS

Lacy, S. et al., Drug Metab Dispo. 2015 vol. 43 pp. 1190-1207.*
International Search Report for PCT/US2014/030524, mailed Jul. 17, 2014.

* cited by examiner

METABOLITES OF N-{4-([6,7-BIS(METHYLOXY)QUINOLIN-4-YL]OXY}PHENYL)-N'-(4-FLUOROPHENYL)CYCLOPROPANE-1,1-DICARBOXAMIDE

CROSS-REFERENCE TO RELATED APPLICATIONS

This application is a United States National Phase filing of PCT/US2014/030524, filed Mar. 17, 2014, which claims the benefit of U.S. Provisional Application No. 61/792,413 filed Mar. 15, 2013, the entire contents of which are incorporated herein by reference.

TECHNICAL FIELD

This disclosure relates to metabolites of N-(4-{[6,7-bis(methyloxy)quinolin-4-yl]oxy}phenyl)-N'-(4-fluorophenyl)cyclopropane-1,1-dicarboxamide, a c-Met inhibitor.

BACKGROUND

Traditionally, dramatic improvements in the treatment of cancer are associated with identification of therapeutic agents acting through novel mechanisms. One mechanism that can be exploited in cancer treatment is the modulation of protein kinase activity because signal transduction through protein kinase activation is responsible for many of the characteristics of tumor cells. Protein kinase signal transduction is of particular relevance in, for example, thyroid, gastric, head and neck, lung, breast, prostate, and colorectal cancers, as well as in the growth and proliferation of brain tumor cells.

Protein kinases can be categorized as receptor type or non-receptor type. Receptor-type tyrosine kinases are comprised of a large number of transmembrane receptors with diverse biological activity. For a detailed discussion of the receptor-type tyrosine kinases, see Plowman et al., DN&P 7(6): 334-339, 1994. Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases, including, for example, immunological disorders, cardiovascular diseases, inflammatory diseases, and degenerative diseases. Therefore, protein kinases are attractive targets for small molecule drug discovery. Particularly attractive targets for small-molecule modulation with respect to antiangiogenic and antiproliferative activity include receptor type tyrosine kinases Ret, c-Met, and VEGFR2.

The kinase c-Met is the prototypic member of a subfamily of heterodimeric receptor tyrosine kinases (RTKs) which include Met, Ron, and Sea. The endogenous ligand for c-Met is the hepatocyte growth factor (HGF), a potent inducer of angiogenesis. Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See Maulik et al, Cytokine & Growth Factor Reviews, 2002, 13, 41-59). c-Met, VEGFR2, and/or Ret overexpression has been demonstrated on a wide variety of tumor types, including breast, colon, renal, lung, squamous cell myeloid leukemia, hemangiomas, melanomas, and astrocytic tumor (which includes glioblastoma, giant cell glioblastoma, gliosarcoma, and glioblastoma with oligodendroglial components). The Ret protein is a transmembrane receptor with tyrosine kinase activity. Ret is mutated in most familial forms of medullary thyroid cancer. These mutations activate the kinase function of Ret and convert it into an oncogenic form.

Accordingly, small-molecule compounds that specifically inhibit, regulate, and/or modulate the signal transduction of kinases, particularly including Ret, c-Met, and VEGFR2 described above, are particularly desirable as a means to treat or prevent disease states associated with abnormal cell proliferation and angiogenesis. One such small-molecule is XL184, known variously as N-(4-{[6,7-bis(methyloxy)quinolin-4-yl]oxy}phenyl)-N'-(4-fluorophenyl)cyclopropane-1,1-dicarboxamide and by the name cabozantinib (COMETRIQ™), which is the L-malate salt of cabozantinib. Cabozantinib has the chemical structure:

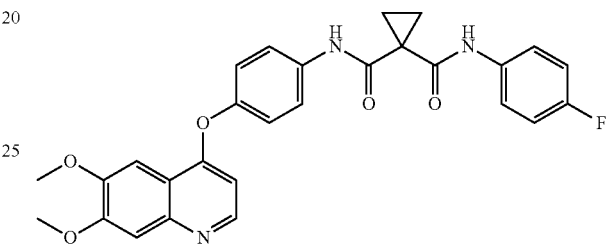

In November, 2012, cabozantinib achieved regulatory approval in the United States for the treatment of progressive metastatic medullary thyroid cancer. Other clinical trials of cabozantinib are ongoing.

WO 2005/030140 describes the synthesis of cabozantinib (Example 48) and also discloses the therapeutic activity of this molecule to inhibit, regulate, and/or modulate the signal transduction of kinases, (Assays, Table 4, entry 289). Example 48 is on paragraph [0353] in WO 2005/030140.

A need remains for identifying compounds that exhibit a similar activity profile to cabozantinib.

SUMMARY OF THE INVENTION

These and other needs are met by the present invention, which is directed to metabolites of cabozantinib.

In one embodiment of this aspect, the metabolite is a compound of formula Ia

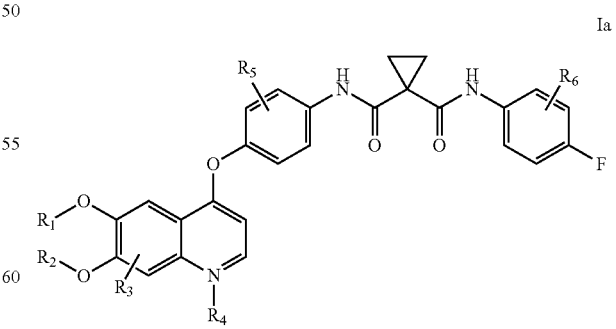

having one or more of the following attributes:
a) one of $R_1$ or $R_2$ is H, $SO_3H$, or a glucuronic acid moiety, and the other is Me;
b) $R_3$ is OH or $OSO_3H$;

c) $R_4$ is $O^-$, provided that when $R_4$ is $O^-$, N is $N^+$;

d) $R_5$ is OH, or $OSO_3H$; and e) $R_6$ is OH or $OSO_3H$.

In another embodiment of this aspect, the metabolite is a compound of formula Ib

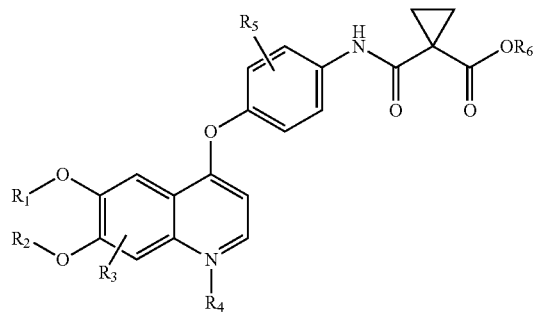

wherein:

a) $R_1$ or $R_2$ are Me; or one of $R_1$ or $R_2$ is H, $SO_3H$, or a glucuronic acid moiety, and the other is Me;

b) $R_3$ is H, OH, or $OSO_3H$;

c) $R_4$ is absent or is $O^-$, provided that when $R_4$ is $O^-$, N is $N^+$; and d) $R_6$ is H or Me.

In another embodiment of this aspect, the metabolite is a compound of formula Ic

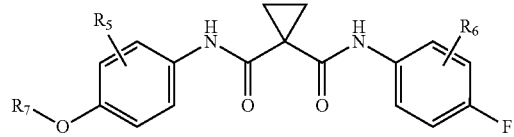

wherein:

a) $R_5$ is OH or $OSO_3H$; and b) $R_6$ is OH or $OSO_3H$; and c) $R_7$ is H, $SO_3H$, or a glucuronic acid moiety.

In one aspect, the invention is directed to an isolated metabolite of cabozantinib having formula Ia, Ib, or Ic.

In one embodiment, the metabolite of cabozantinib is selected from:

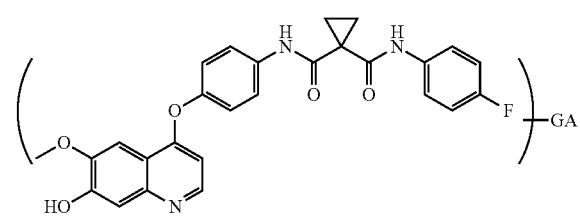

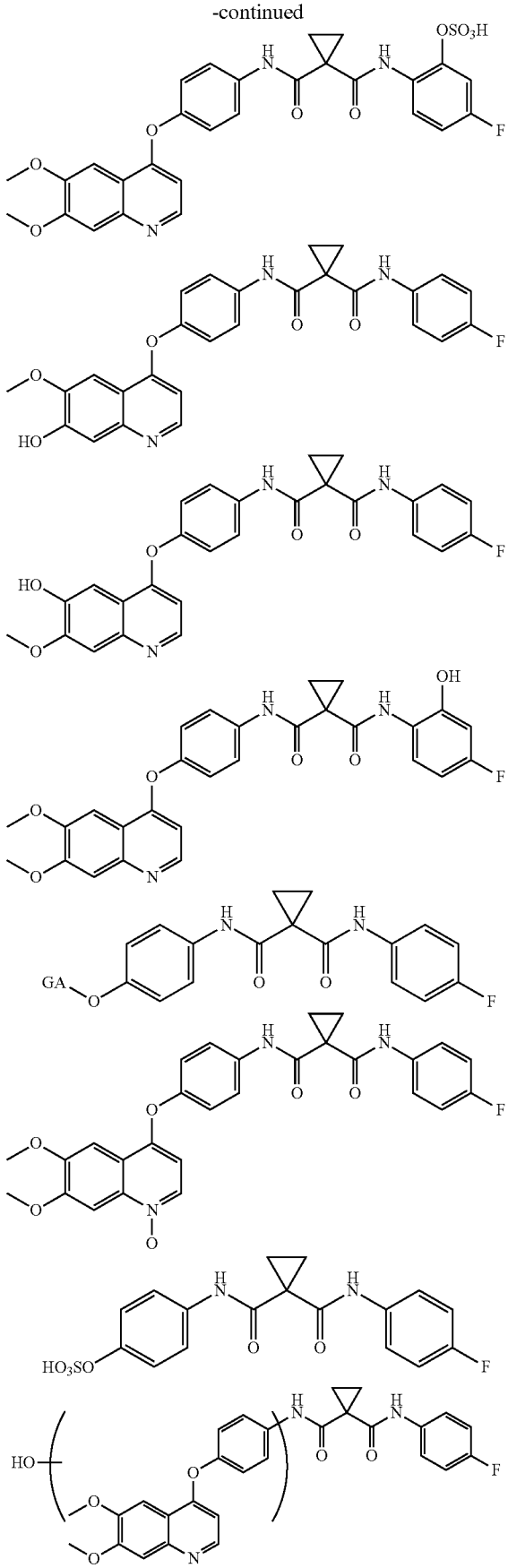

-continued
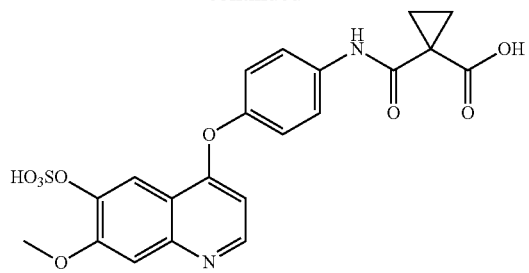
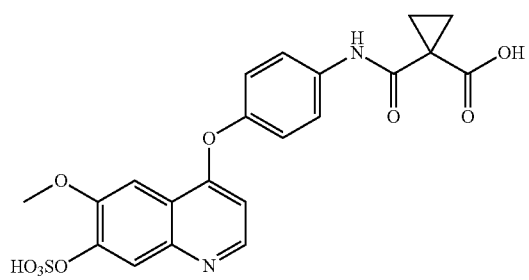
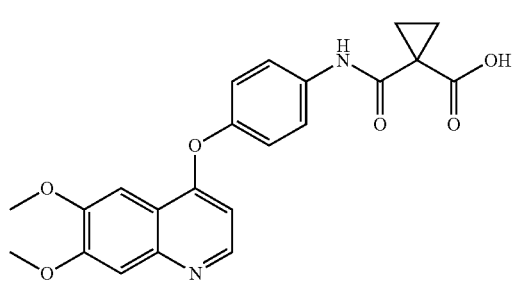
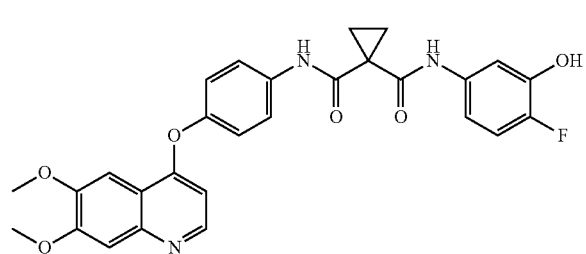
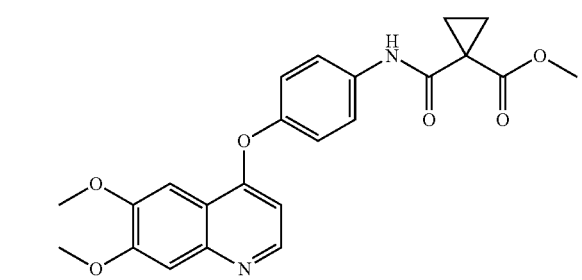
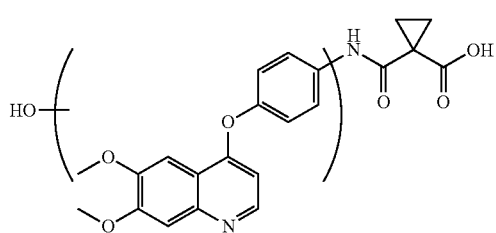
and
-continued
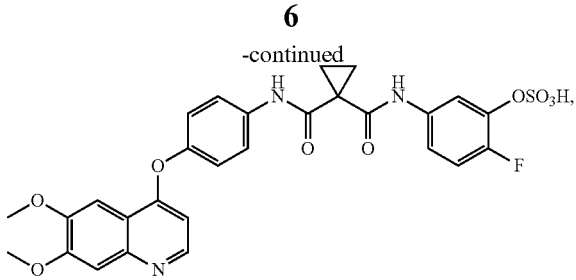
wherein GA is a glucuronic acid moiety such as in, for example,
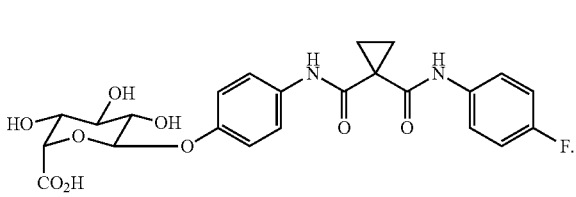 [SMILES: O=C(O)C1OC(Oc2ccc(NC(=O)C3(C(=O)Nc4ccc(F)cc4)CC3)cc2)C(O)C(O)C1O]
In another aspect, the invention is directed to a compound which is selected from:
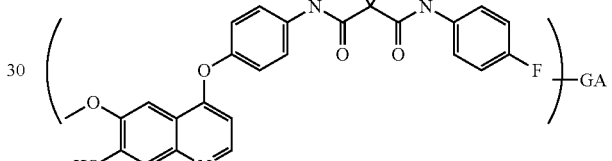
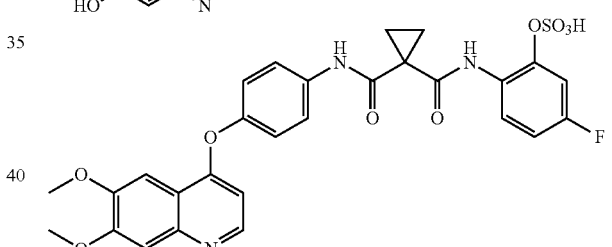
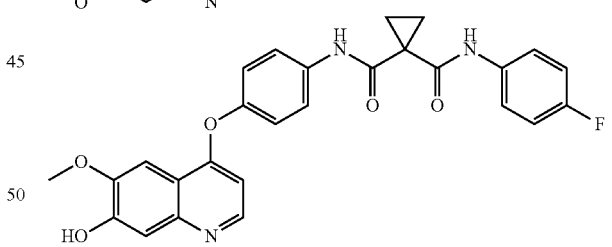
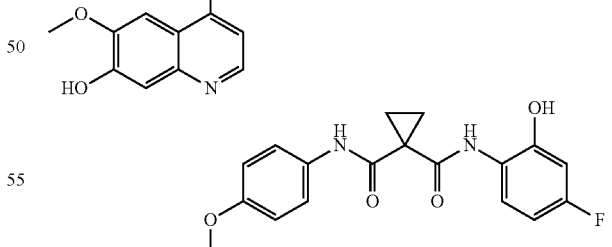
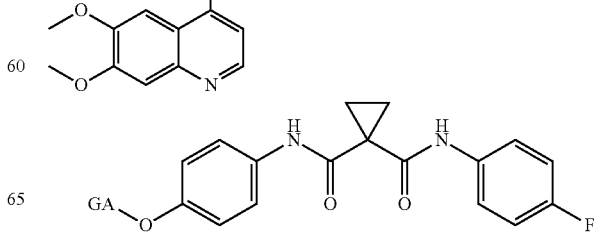

7
-continued

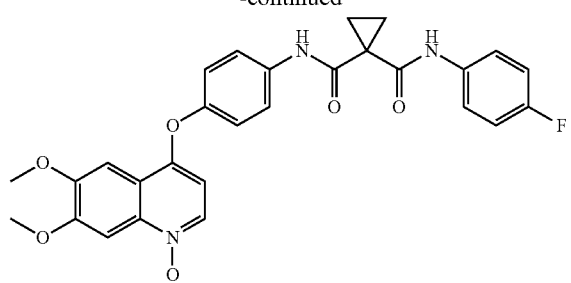

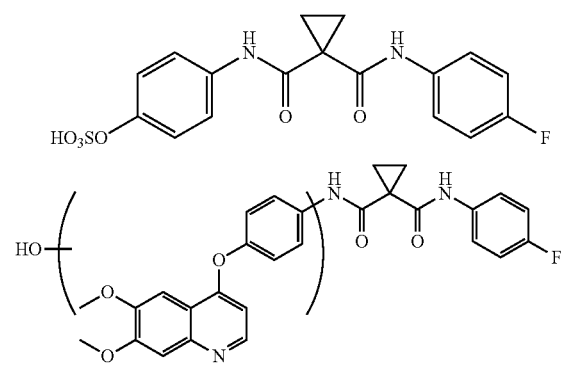

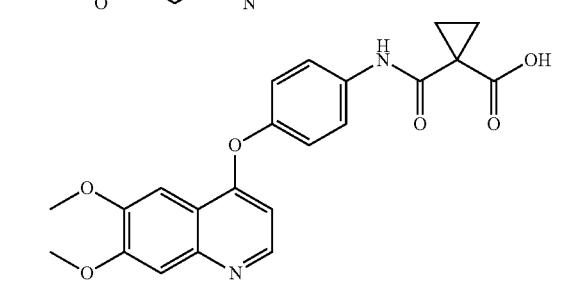

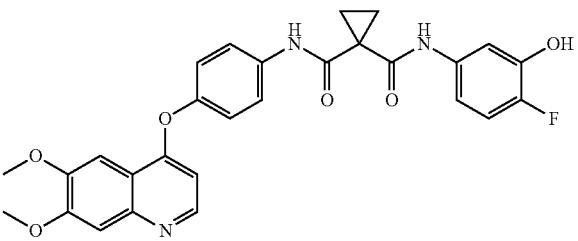

8
-continued

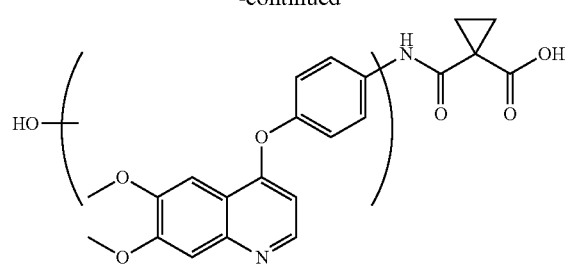

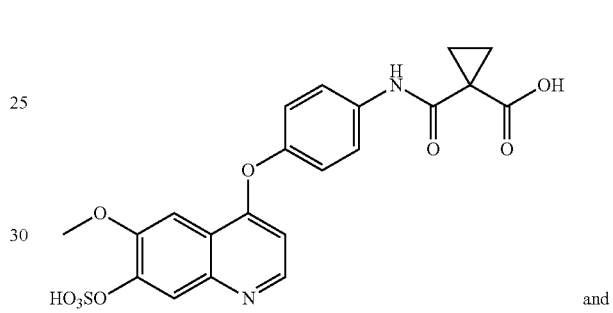

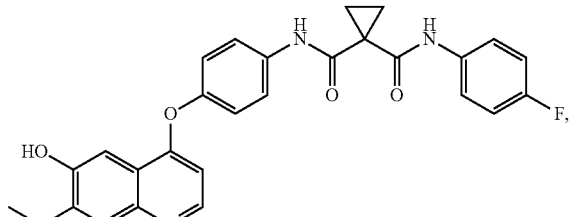

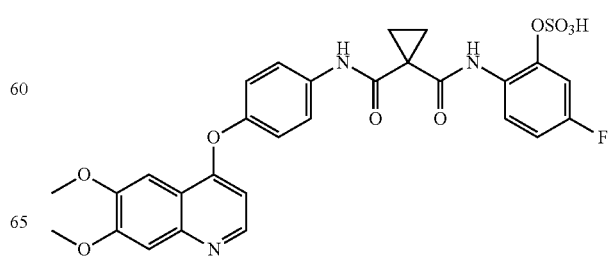

wherein GA is a glucuronic acid moiety.

In another aspect, the invention is directed to a method of treating diseases or disorders associated with uncontrolled, abnormal, and/or unwanted cellular activities, the method comprising administering, to a mammal in need thereof, a therapeutically effective amount of a compound which is a metabolite of cabozantinib. In one embodiment, the metabolite is selected from:

-continued
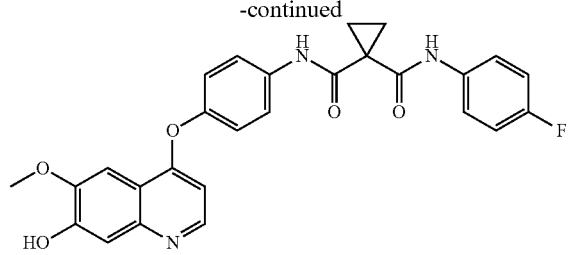
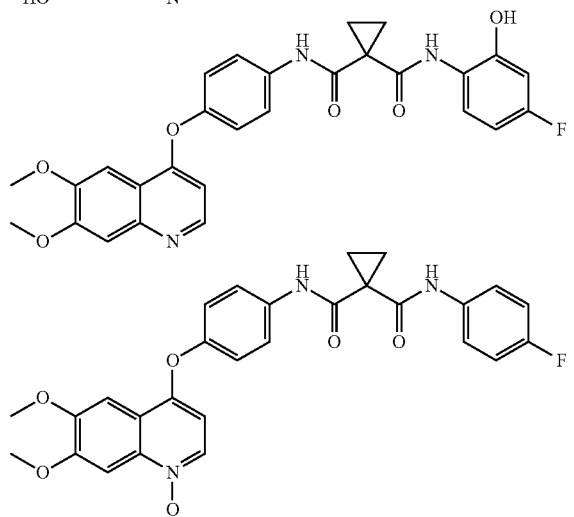
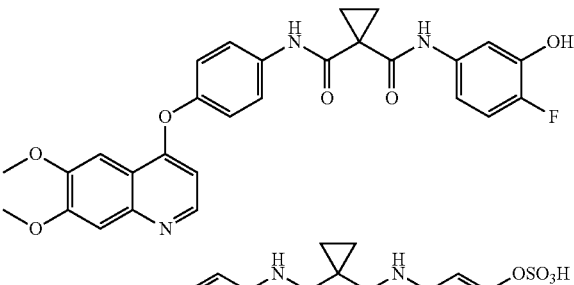
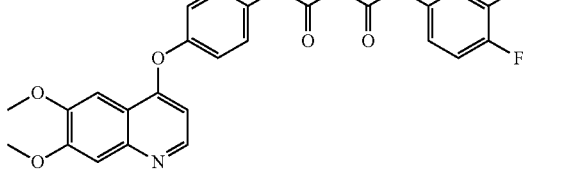
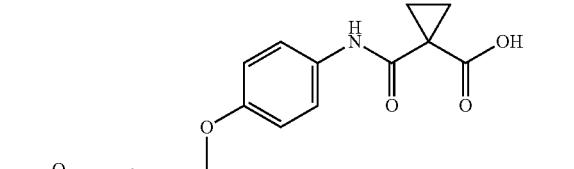
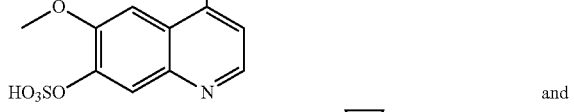
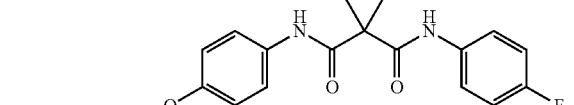
and
or a pharmaceutically acceptable salt thereof.
In another aspect, the invention is directed to a pharmaceutical composition comprising a therapeutically active metabolite of cabozantinib and at least one pharmaceutically acceptable carrier. In one embodiment, the metabolite is selected from:
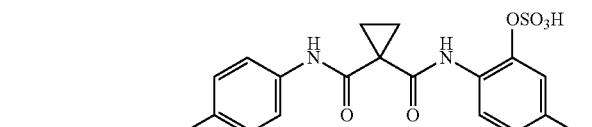
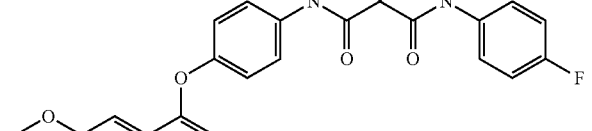
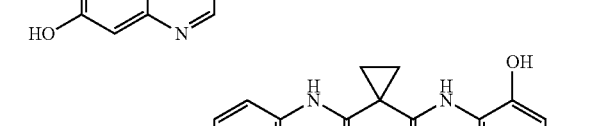
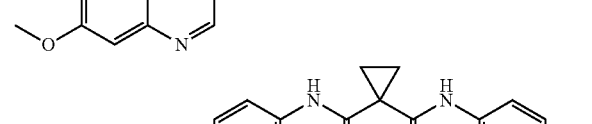
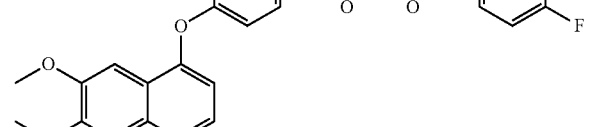
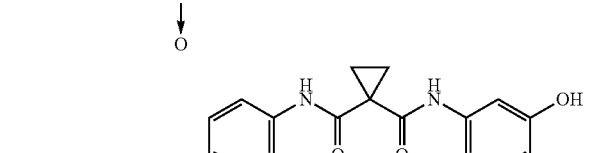

-continued

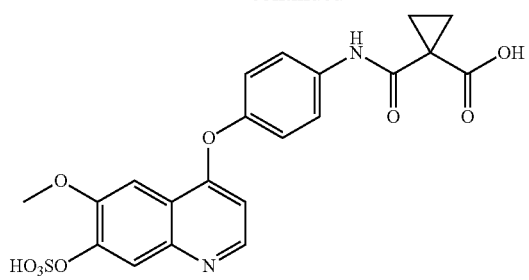

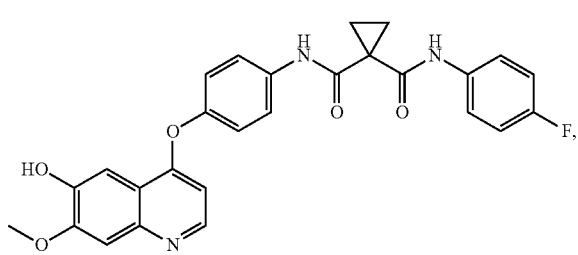

or a pharmaceutically acceptable salt thereof and at least one pharmaceutically acceptable carrier.

In another aspect the invention is directed to a method for identifying a metabolite of cabozantinib, comprising:

administering cabozantinib to a mammal;

detecting or measuring a level or concentration of a metabolite of cabozantinib in a mammal in tissues or bodily fluids of the mammal;

wherein the metabolite is selected from the group consisting of:

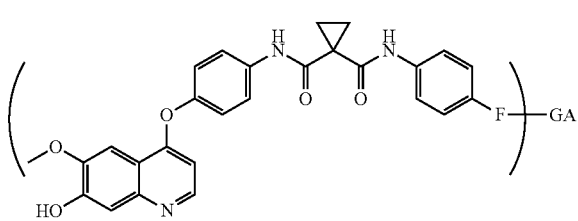

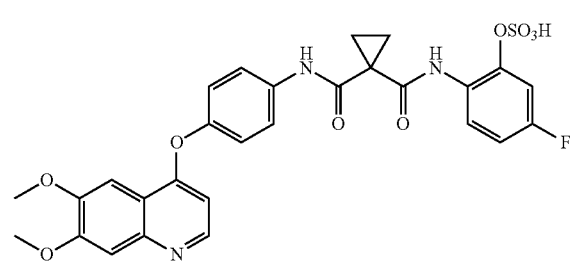

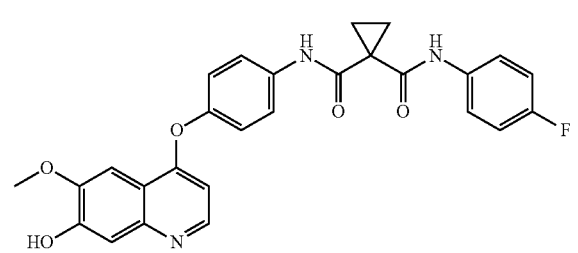

-continued

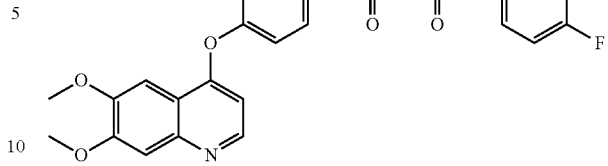

and

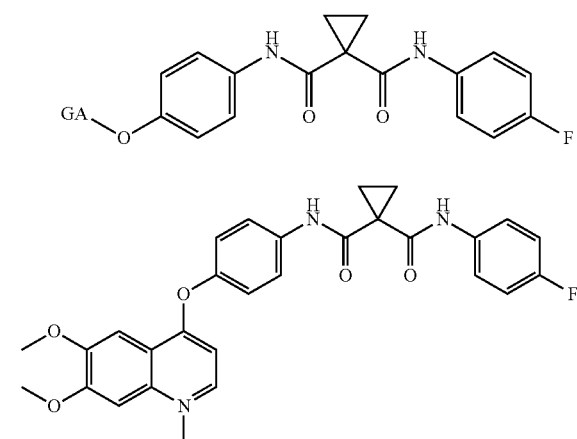

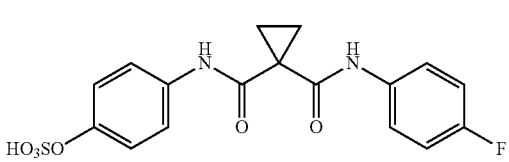

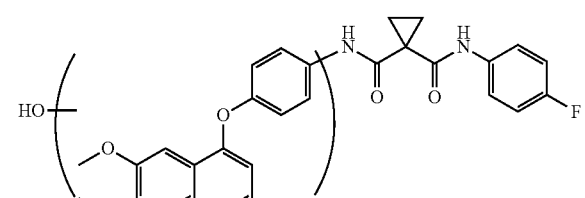

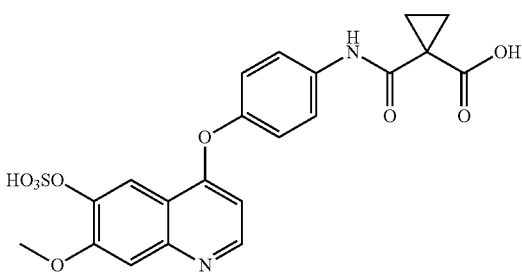

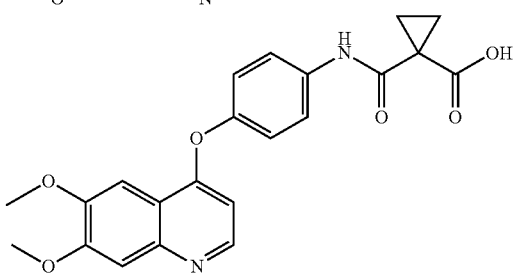

-continued

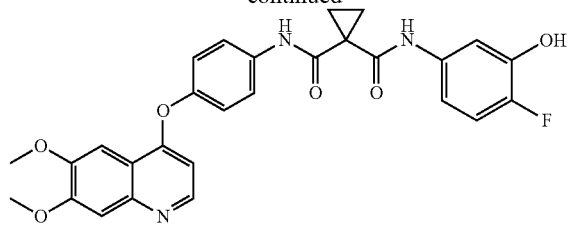

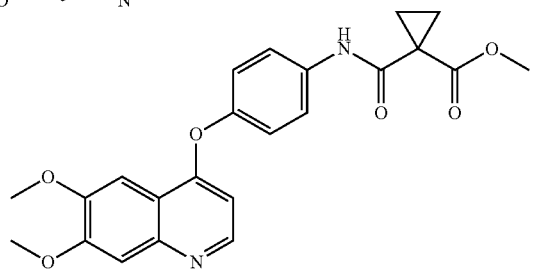

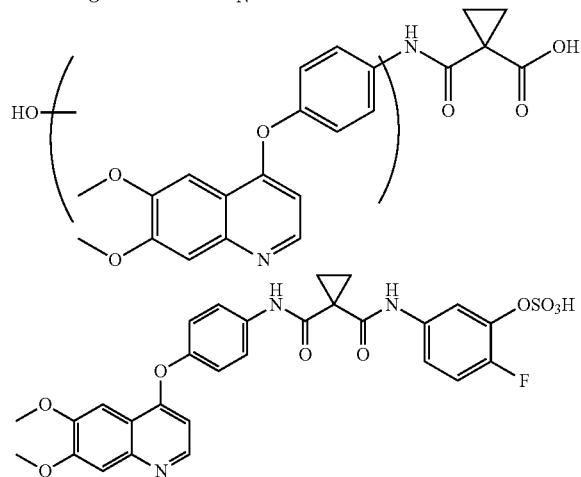

and

-continued

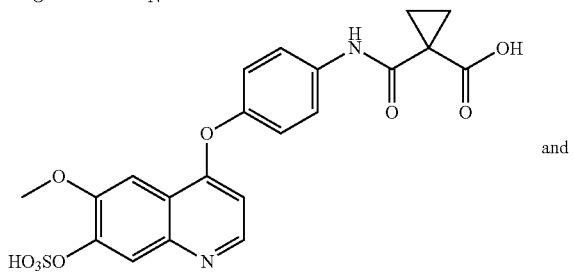

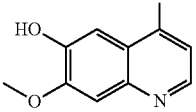

wherein GA is a glucuronic acid moiety.

The compounds may additionally be used in other methods; for example, in bioassay methods for determining the kinase inhibitory activity of test compounds or as internal standards in related methods.

DETAILED DESCRIPTION OF THE INVENTION

In one aspect, the invention is directed to metabolites of cabozantinib, particularly human metabolites. Thus, the metabolites may be referred to hereinafter as "human metabolites." Human metabolites of cabozantinib include metabolites of cabozantinib that were formed in the bodies of human subjects after ingestion or application of cabozantinib according to clinical protocols regarding dosing and monitoring, including those described herein. In various embodiments, the term encompasses molecular species formed in vivo, whether or not the species is even detected or analyzed in a particular trial. It is also contemplated that some metabolites are unique to particular individuals, reflecting different genetic make-up and the presence and activity of various enzymes, including cytochrome P450 and UGT enzymes which are involved in metabolism. Thus, human metabolites cover all such metabolites formed in the human body.

Some human metabolites are depicted in Scheme 1. These human metabolites were identified during clinical studies of cabozantinib, which appears as compound I in Scheme 1, by metabolic profiling, particularly from human plasma, urine, and feces.

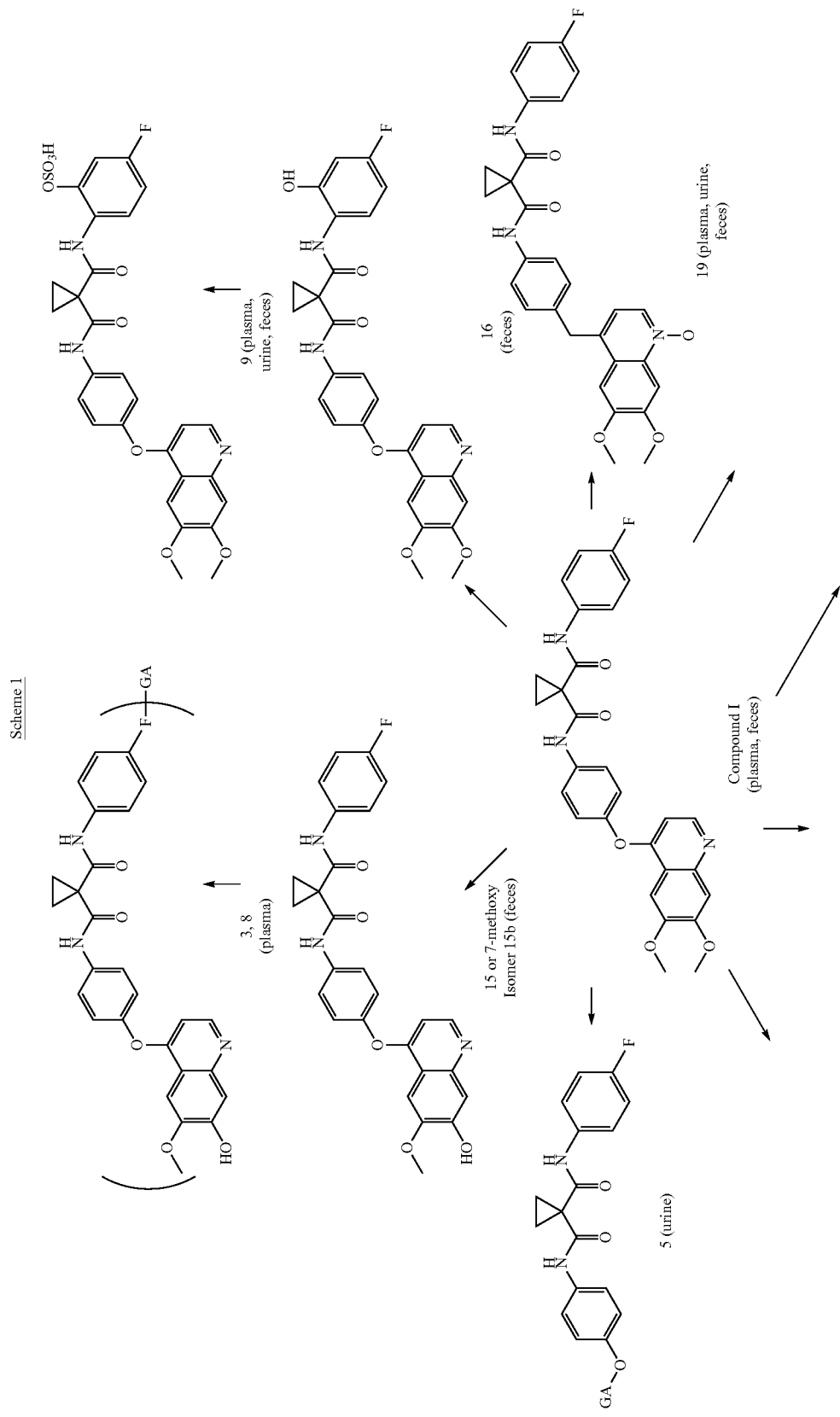

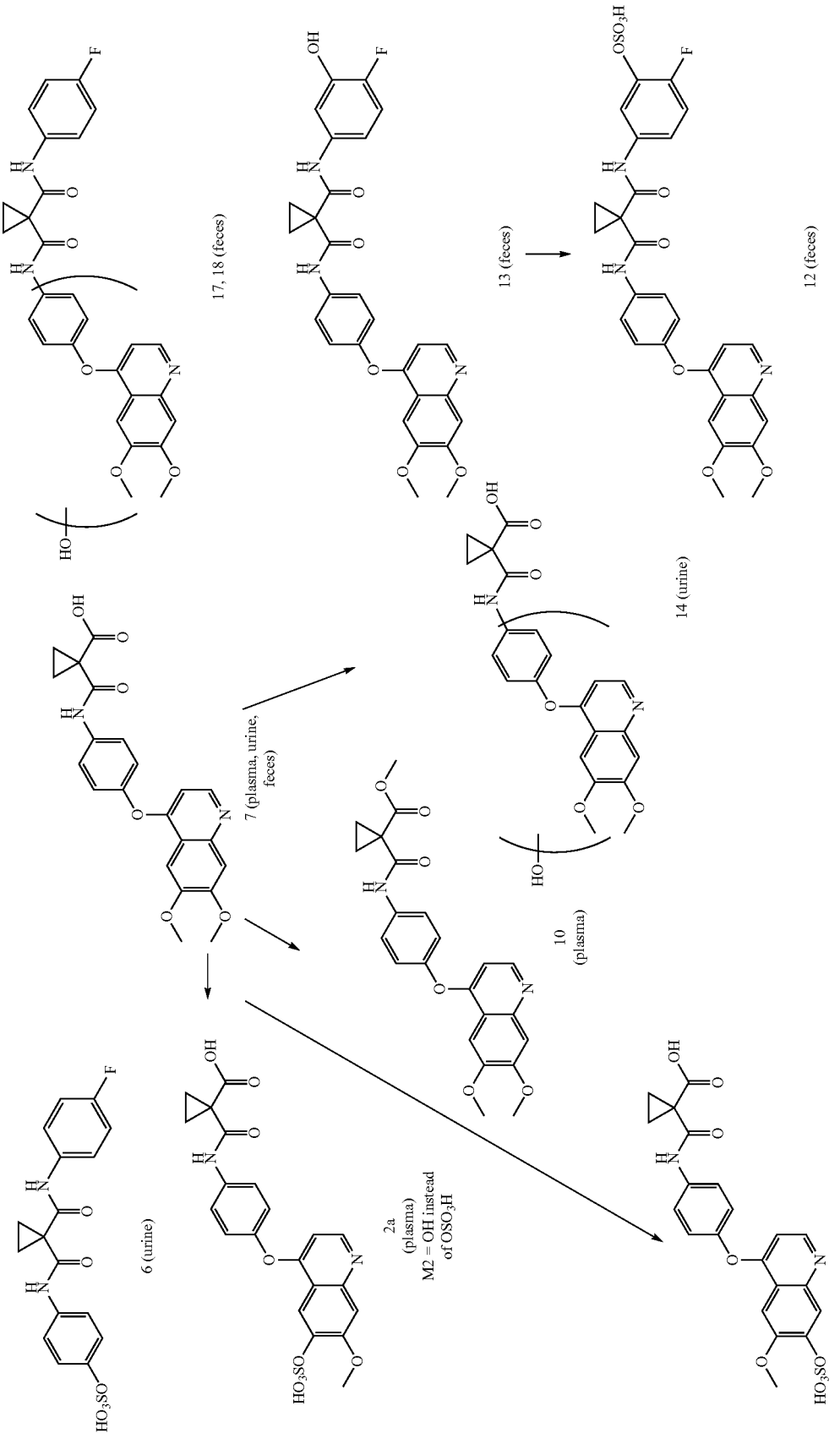
GA: glucuronic acid moiety *M2b, 7-demethyl half-dimer sulfate, is an isomer of M2a, In various embodiments, the cabozantinib metabolites, including those depicted in Scheme 1, are isolated from body tissues and fluids, and/or are prepared synthetically according to methods available to the skilled artisan. A variety of separation processes can be carried out on tissue and fluid samples to provide samples for further analysis, such as nuclear magnetic resonance, gas chromatography (GC), liquid chromatography (LC), and mass spectrometry. In such samples, the metabolites are contained in compositions that are essentially lacking in the presence of any of the other metabolites. The presence of the metabolites can be quantified by physical methods, such as the measurement of nuclear decay from radioactive isotopes, measurement of index of refraction, flame ionization, ionization and deflection in magnetic fields, ultraviolet (UV absorption), and the like.

In various embodiments, the human metabolites are provided in crystalline or solution forms that have considerable degrees of purity. Organic synthetic routes are available for preparing the compounds in relative pure form, for example, in purities of 80 percent or greater, 90 percent or greater, 95 percent or greater, or 99 percent or greater. Recrystallization and other purification methods can be carried out to provide compounds that are essentially 100 percent pure. Such synthetic methods and purification techniques are known in the art.

In various embodiments, the metabolites are provided in substantially pure form. "Substantially pure" means that metabolites are pure enough for FDA approval and contain essentially no contaminants or other materials. Alternatively, "substantially pure" means a level of impurity that does not adversely or unacceptably affect the properties of the compounds with respect to safety, effectiveness, stability, and other desirable properties.

In one embodiment, the invention is directed to isolated metabolites as depicted in Scheme 1. In this and other embodiments, the metabolite is selected from:

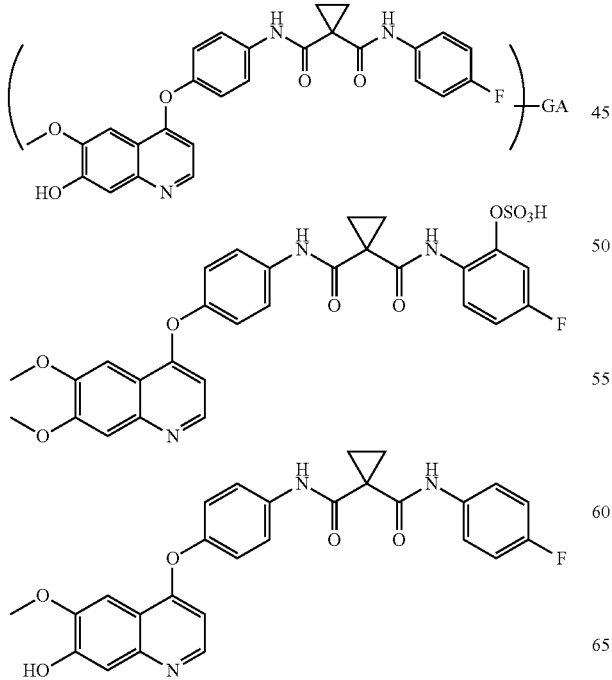

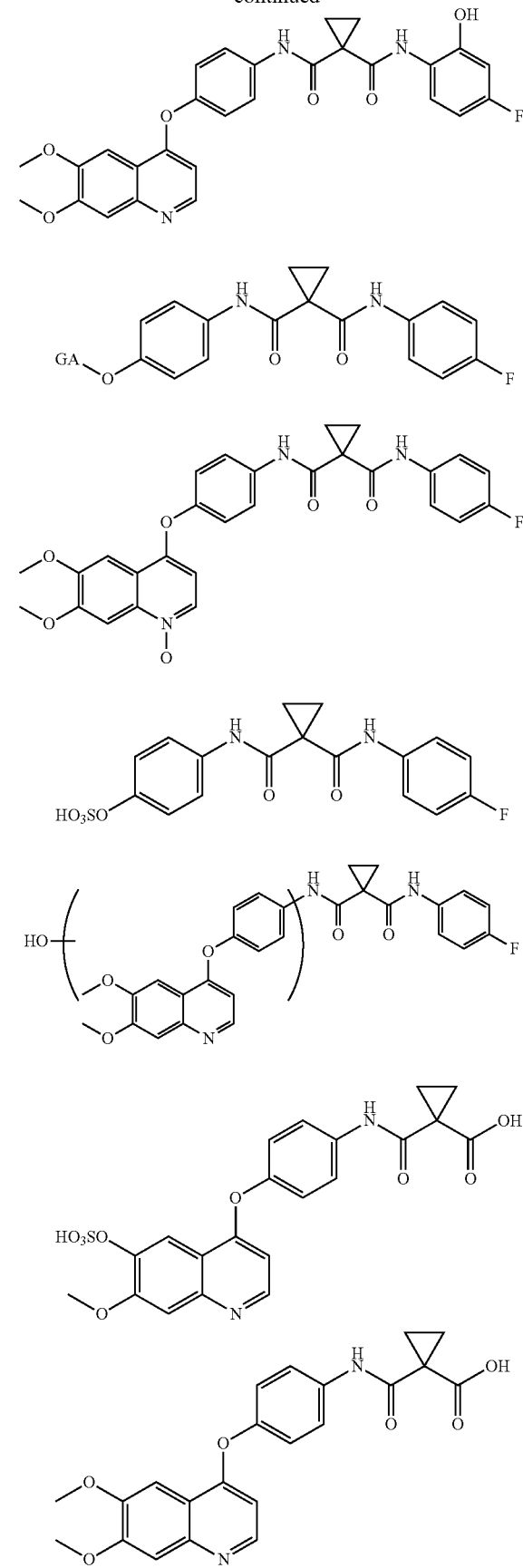

-continued
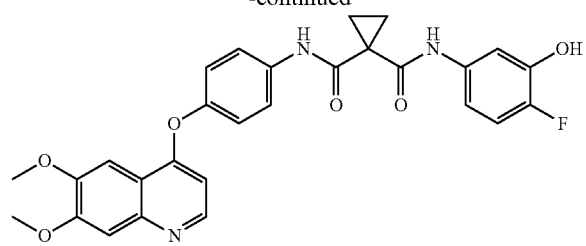
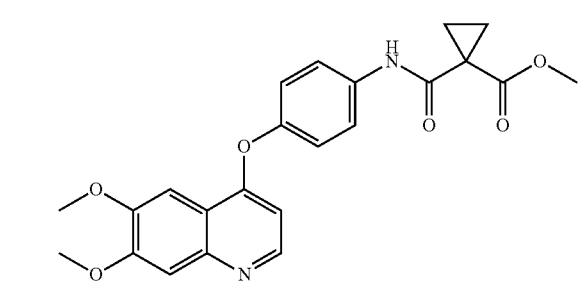
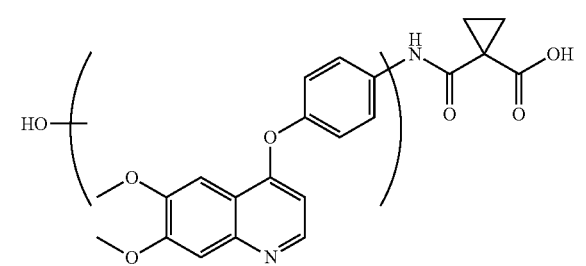
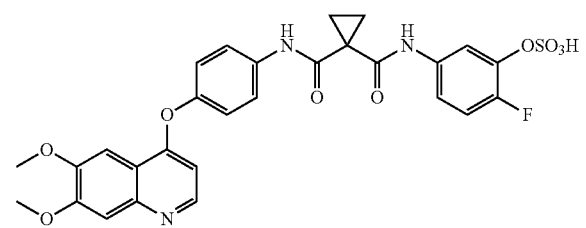
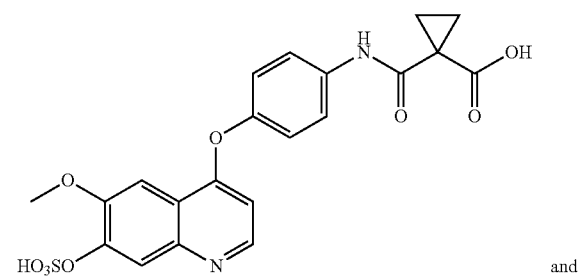
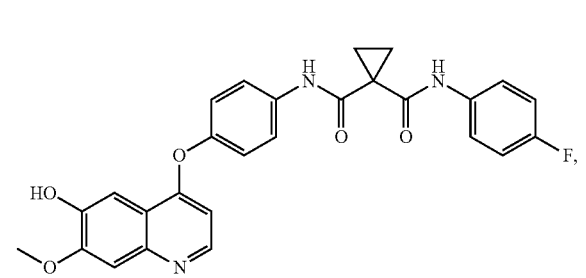 [SMILES: COc1cc2nccc(Oc3ccc(NC(=O)C4(C(=O)Nc5ccc(F)cc5)CC4)cc3)c2cc1O]
and
wherein GA is a glucuronic acid moiety.
More particularly, the metabolite is selected from:
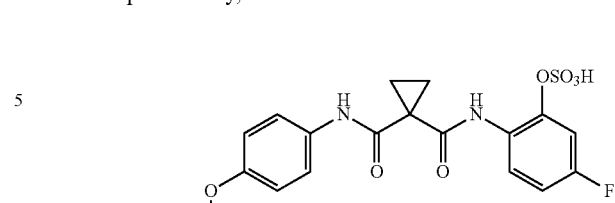
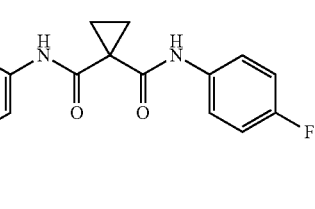
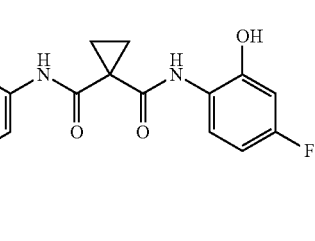
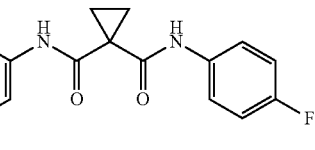
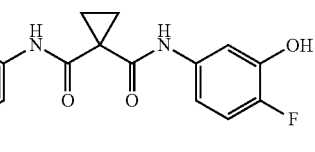
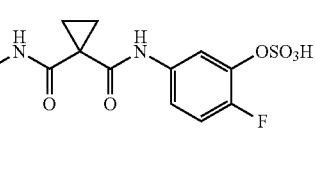

-continued

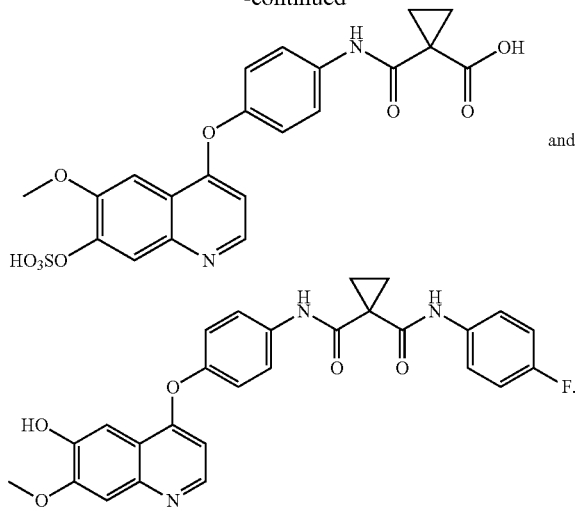

and

In a particular embodiment, the isolated metabolite is

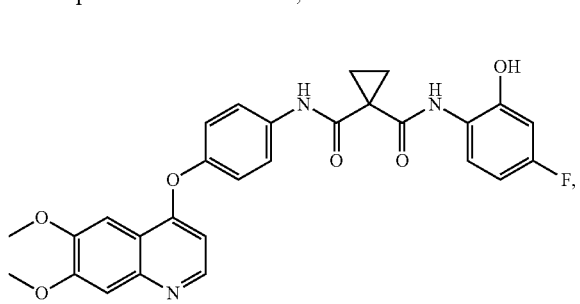

or a pharmaceutically acceptable salt thereof.

In another particular embodiment, the isolated metabolite is

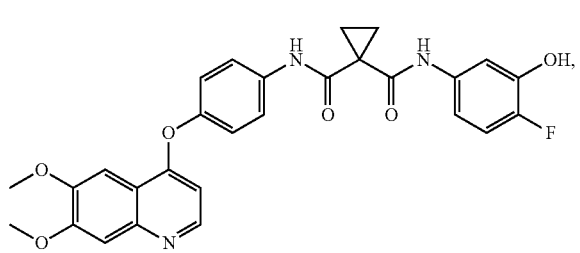 [SMILES: COc1cc2nccc(Oc3ccc(NC(=O)C4(C(=O)Nc5ccc(F)c(O)c5)CC4)cc3)c2cc1OC]

or a pharmaceutically acceptable salt thereof.

In another particular embodiment, the isolated metabolite is

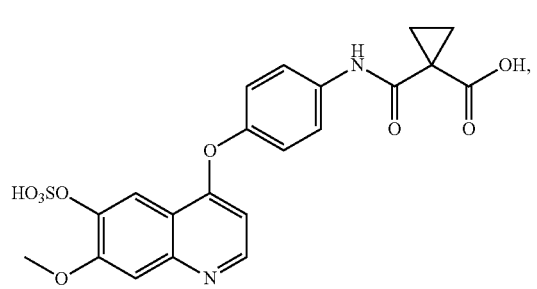

or a pharmaceutically acceptable salt thereof.

In another particular embodiment, the isolated metabolite is or a pharmaceutically acceptable salt thereof.

In another particular embodiment, the isolated metabolite is or a pharmaceutically acceptable salt thereof.

In another particular embodiment, the isolated metabolite is or a pharmaceutically acceptable salt thereof.

In another particular embodiment, the isolated metabolite is or a pharmaceutically acceptable salt thereof.

In another particular embodiment, the isolated metabolite is

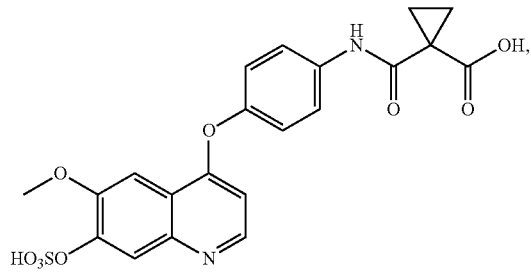

or a pharmaceutically acceptable salt thereof.

Methods of the invention include administering cabozantinib or a cabozantinib metabolite to a mammal such as a human and detecting metabolites by measuring the level of concentration of one of the metabolites in the tissues or bodily fluids of the mammal. Bodily fluids include, without limitation, blood plasma, bile, urine, and feces, while tissues include, without limitation, liver microsomes, hepatocytes, and perfused livers. In various embodiments, the metabolites are isotopically labeled with various isotopes to assist in detection or quantification of the metabolites in the tissues or bodily fluids. Thus, the metabolites include those that are labeled with $^{14}C$ or $^{3}H$ (tritium) for the purpose of detecting or identifying particular metabolites from their nuclear decay products. The metabolites also include metabolites labeled with $^{13}C$ or $^{2}H$ (deuterium) to facilitate nuclear magnetic resonance and/or mass spectrometric analysis of the compounds. As used herein, deuterated means substituted with deuterium, and tritiated means substituted with tritium. In various other embodiments, the metabolites of the invention, as depicted in Scheme 1, also include their salts, tautomers, and isotopically labeled variants (including $^{14}C$, $^{13}C$, $^{3}H$, or $^{2}H$).

More specifically, in one embodiment, the invention provides a method for identifying a metabolite of cabozantinib, comprising:
administering cabozantinib to a mammal;
detecting or measuring a level or concentration of a metabolite of cabozantinib in a mammal in tissues or bodily fluids of the mammal;
wherein the metabolite is selected from the group consisting of

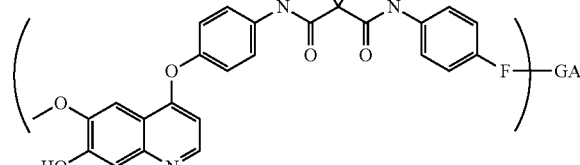

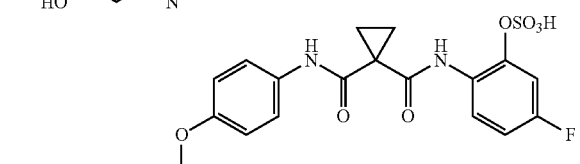

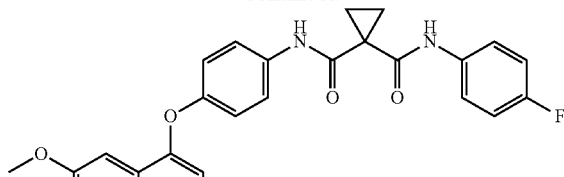

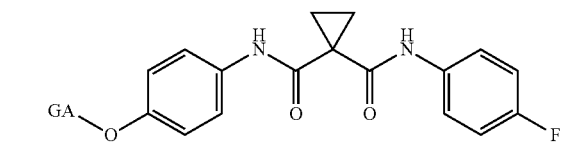

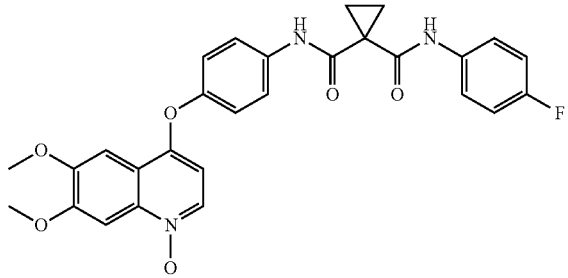

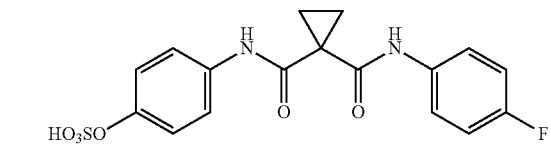

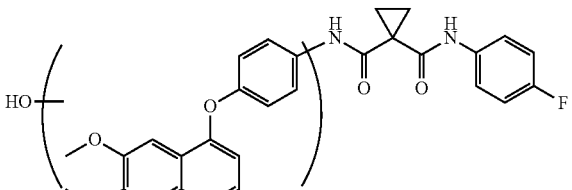

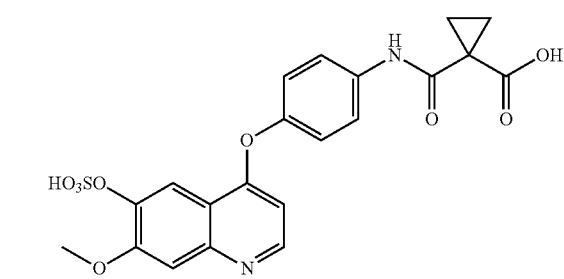

27
-continued
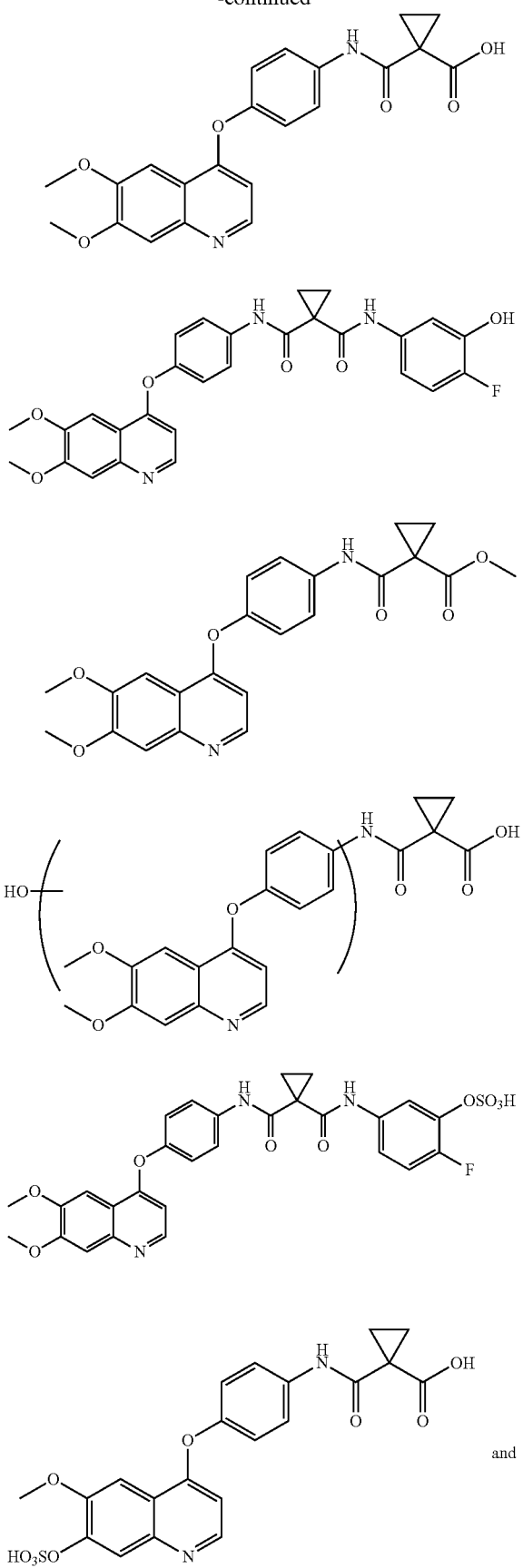
28
-continued
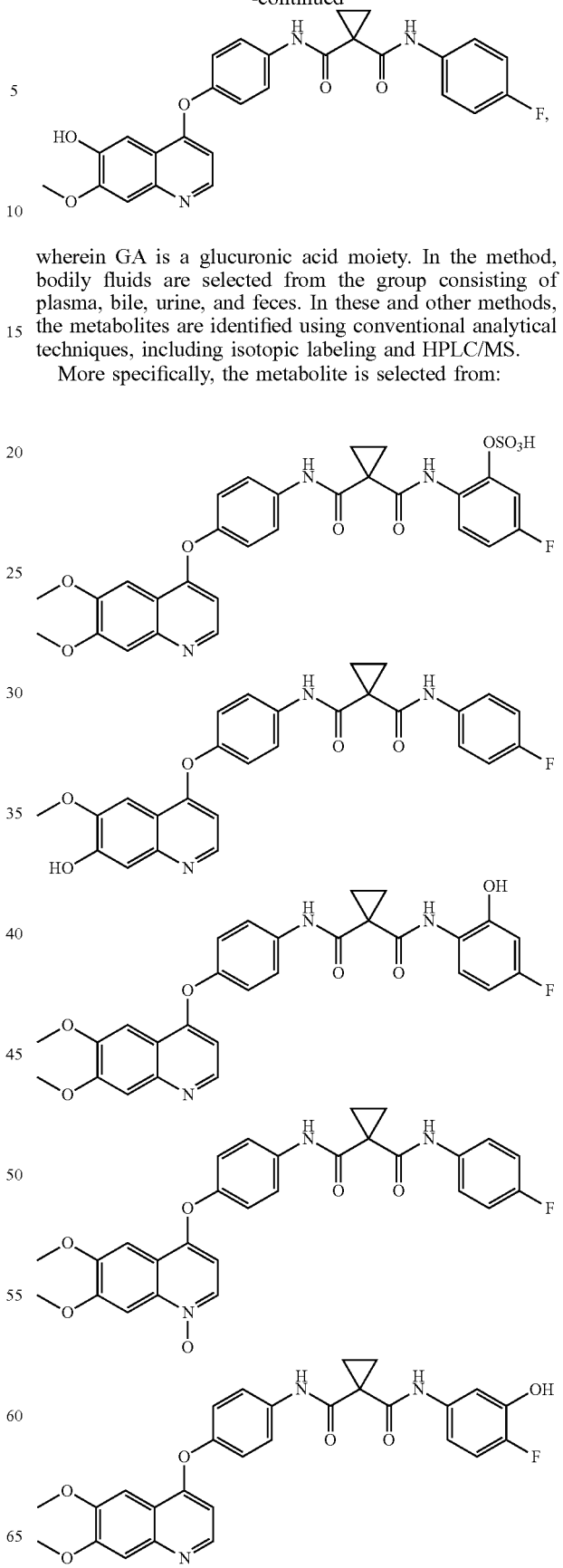
wherein GA is a glucuronic acid moiety. In the method, bodily fluids are selected from the group consisting of plasma, bile, urine, and feces. In these and other methods, the metabolites are identified using conventional analytical techniques, including isotopic labeling and HPLC/MS.
More specifically, the metabolite is selected from:
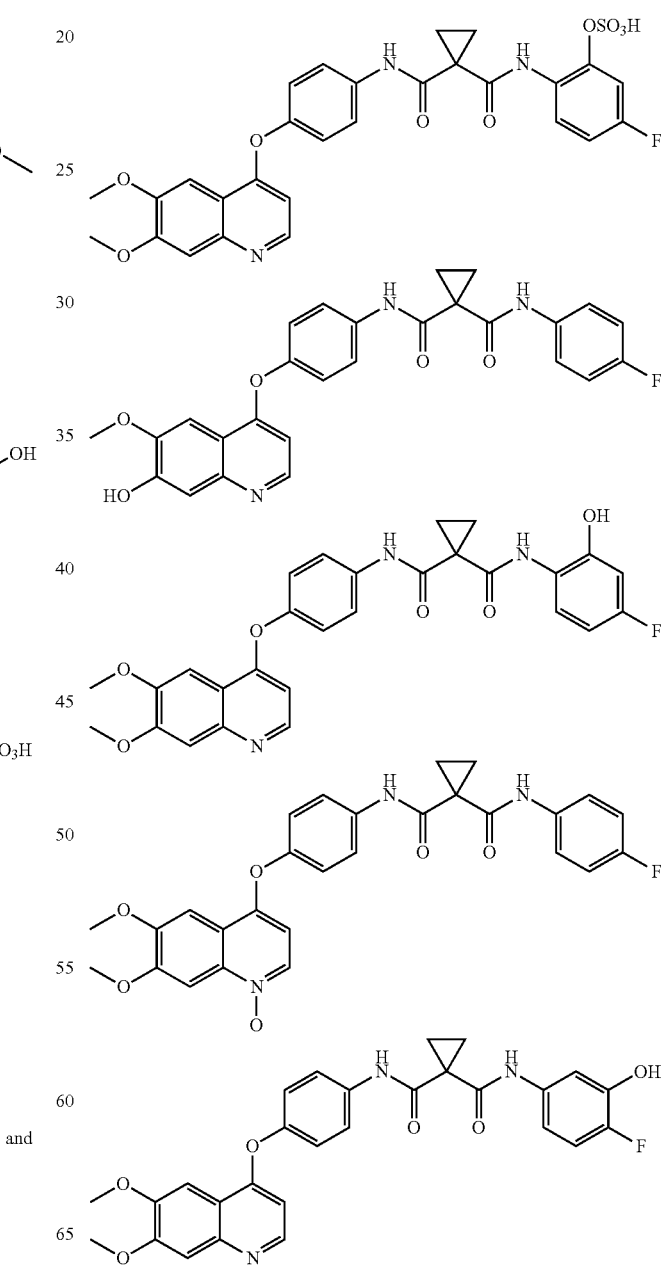

-continued

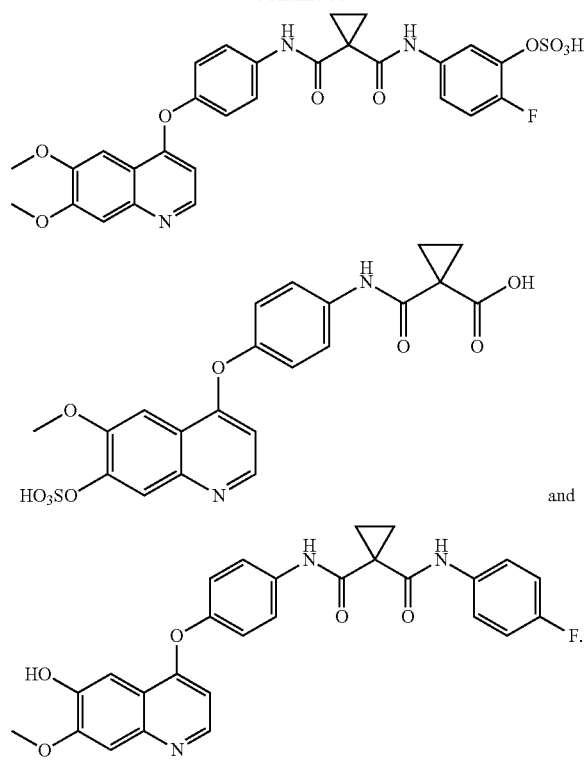

Another aspect of the invention is a method of modulating the in vivo activity of a kinase, the method comprising administering to a subject an effective amount a cabozantinib metabolite, which is a compound selected from:

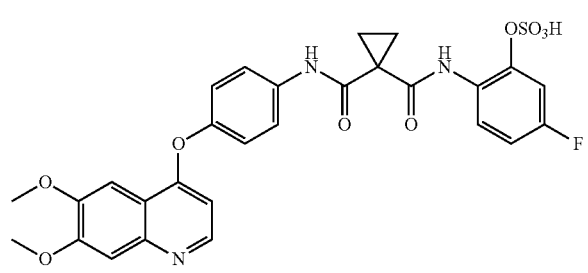

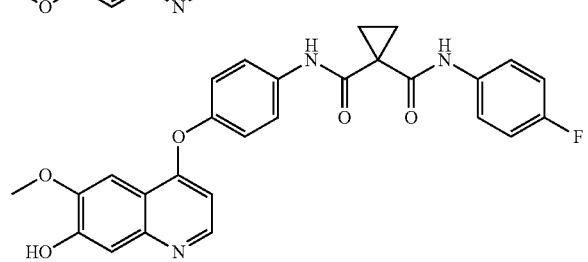

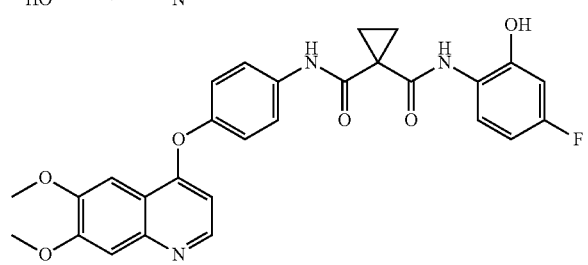

-continued

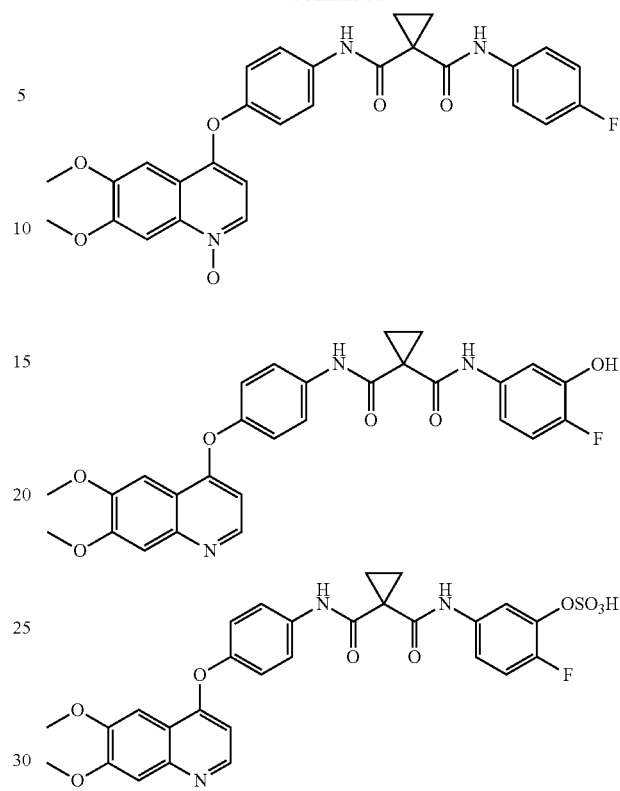

or a pharmaceutical composition comprising such a compound.

In one embodiment of this aspect, modulating the in vivo activity of the kinase comprises inhibition of said kinase.

In another embodiment of this aspect, the kinase is at least one of c-Met, RET, KDR, c-Kit, flt-3, and flt-4.

In another embodiment, the kinase is c-Met.

Another aspect of the invention is directed to a method of treating diseases or disorders associated with uncontrolled, abnormal, and/or unwanted cellular activities, the method comprising administering, to a mammal in need thereof, a therapeutically effective amount of a cabozantinib metabolite, which is a compound selected from:

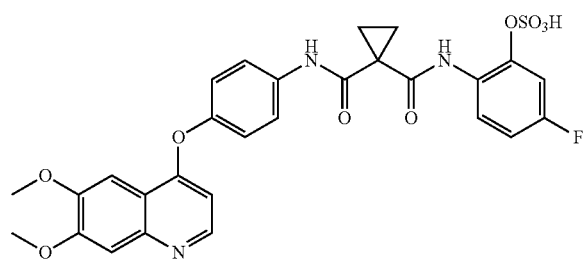
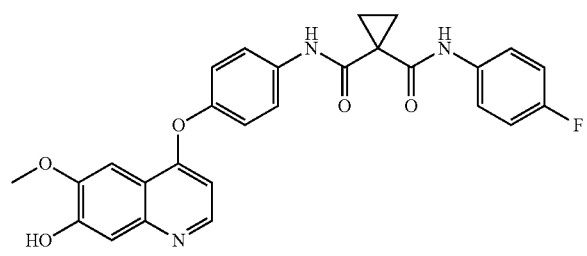
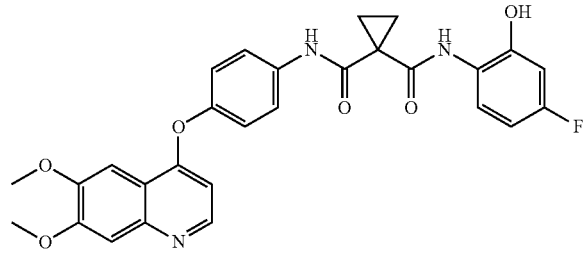
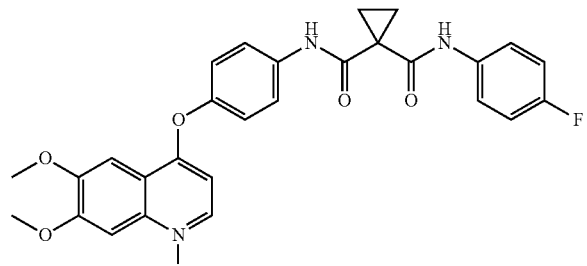
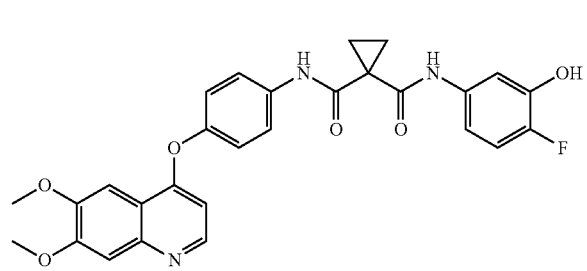
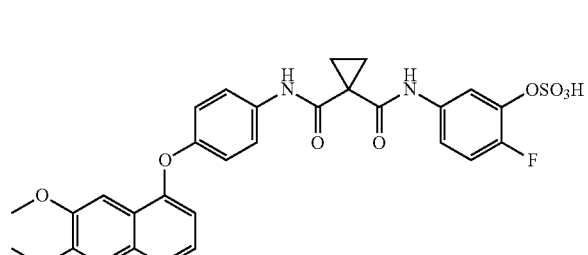
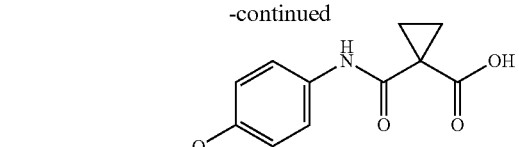
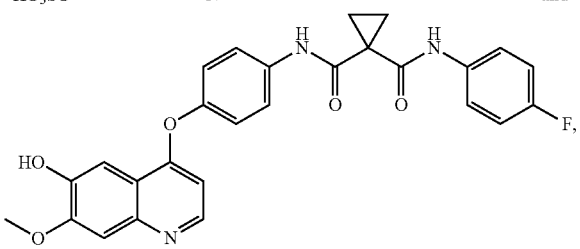
or a pharmaceutical composition comprising such a compound.
In a particular embodiment, the compound is
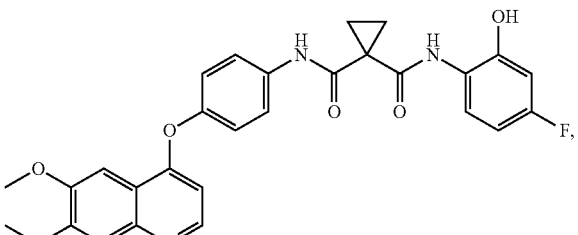
or a pharmaceutically acceptable salt thereof.
In another particular embodiment, the compound is
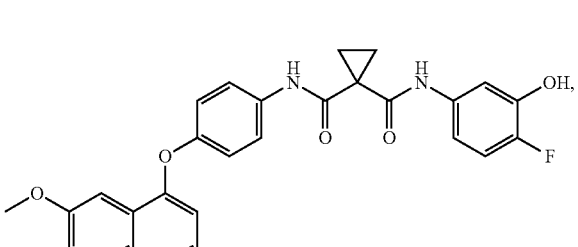
or a pharmaceutically acceptable salt thereof.
In another particular embodiment, the compound is
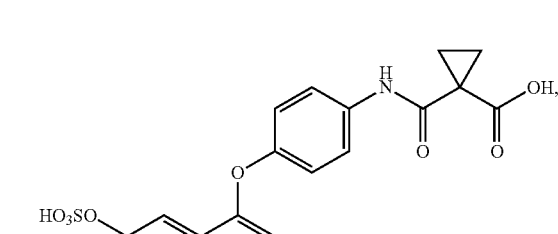
or a pharmaceutically acceptable salt thereof.

In another particular embodiment, the compound is

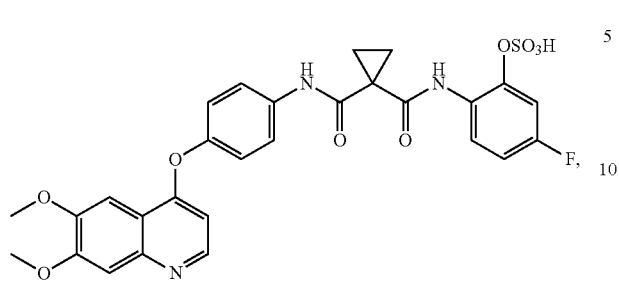

or a pharmaceutically acceptable salt thereof.

In another particular embodiment, the compound is

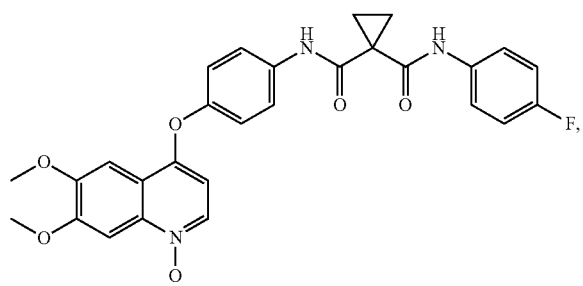

or a pharmaceutically acceptable salt thereof.

In another particular embodiment, the compound is

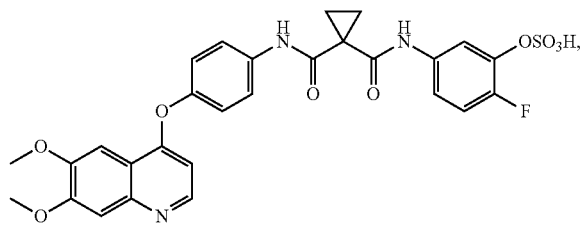

or a pharmaceutically acceptable salt thereof.

In another particular embodiment, the compound is

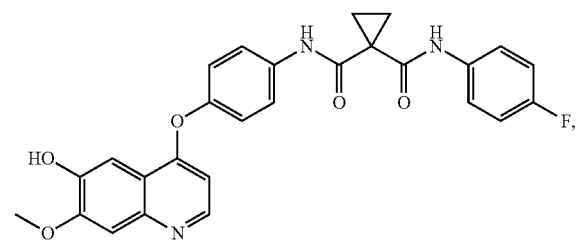 [SMILES: COc1cc2nccc(Oc3ccc(NC(=O)C4(C(=O)Nc5ccc(F)cc5)CC4)cc3)c2cc1O]

or a pharmaceutically acceptable salt thereof.

In another particular embodiment, the compound is

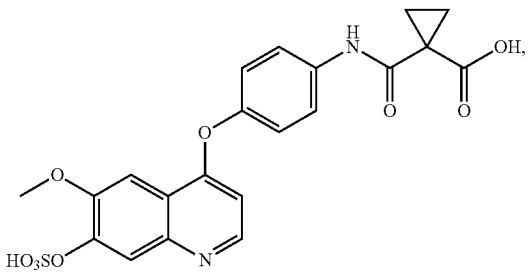

or a pharmaceutically acceptable salt thereof.

In another aspect, the invention is directed to a method of screening for a modulator of a kinase, said kinase selected from c-Met, KDR, RET, c-Kit, flt-3, and flt-4, the method comprising combining a cabozantinib metabolite which is a compound selected from:

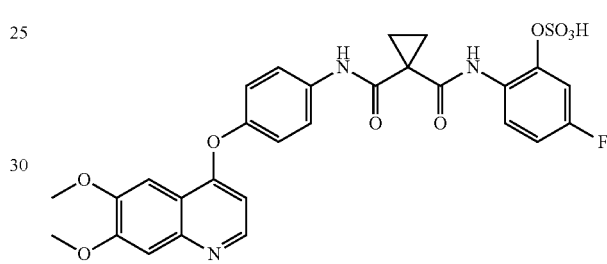

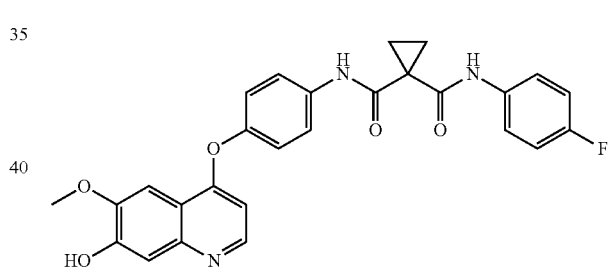

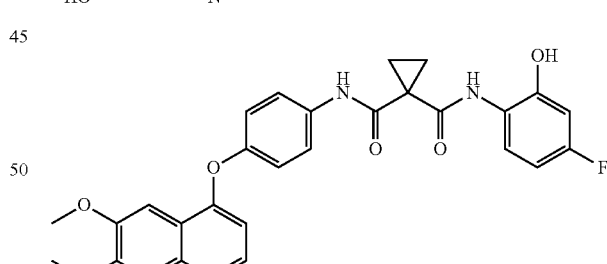

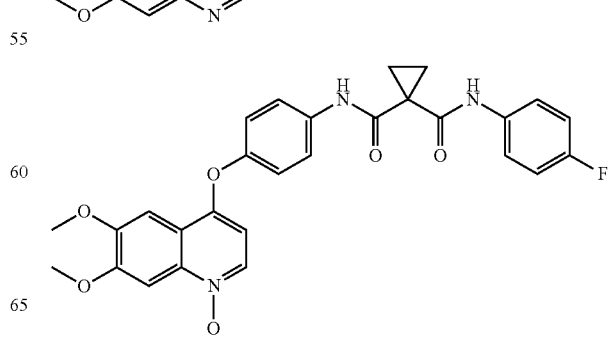

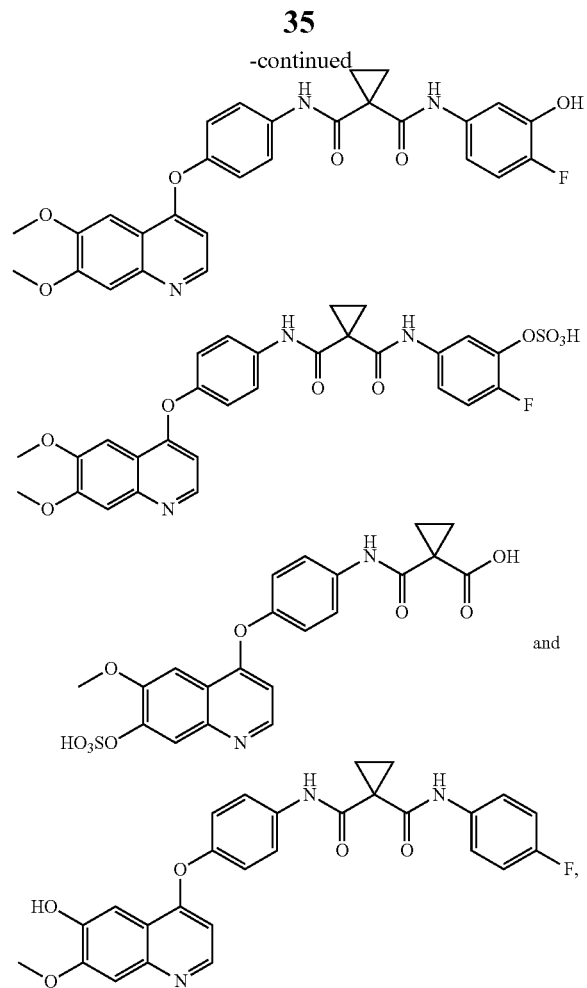

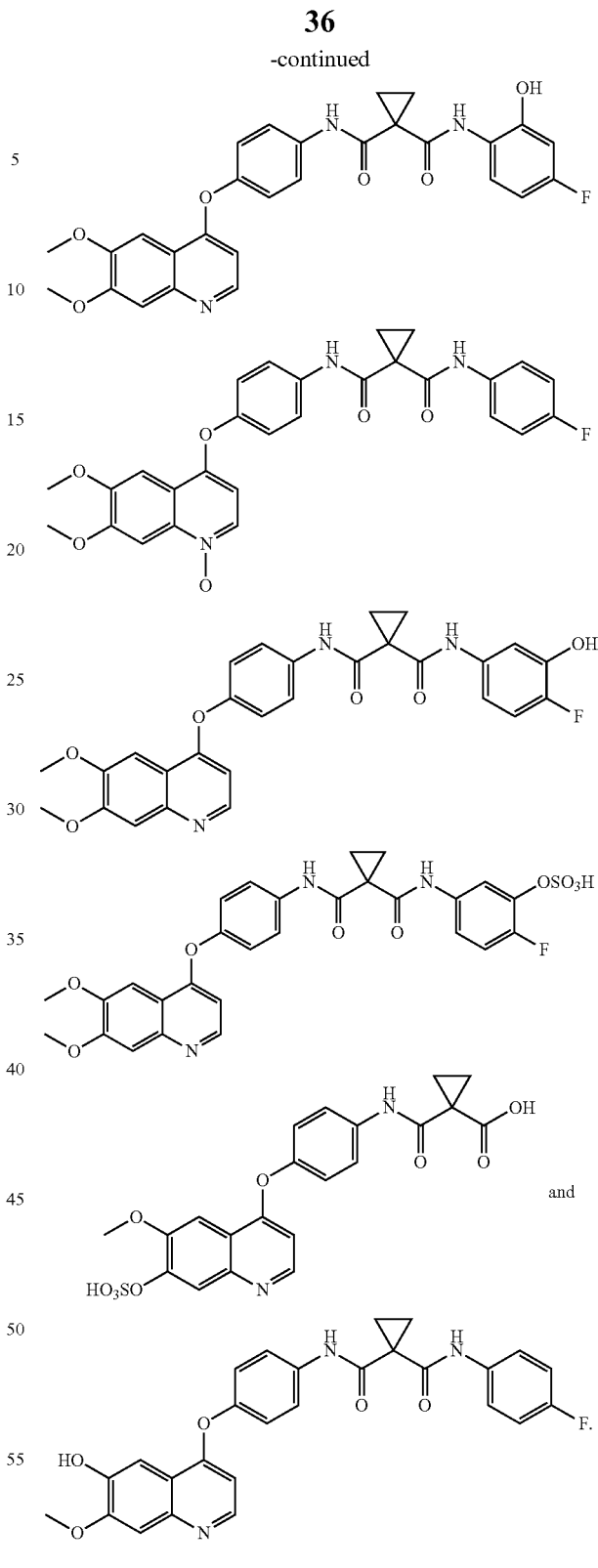

and at least one candidate agent, and determining the effect of the candidate agent on the activity of said kinase.

Another aspect of the invention is directed to a method of inhibiting proliferative activity in a cell, the method comprising administering an effective amount of a composition comprising a compound to a cell or a plurality of cells, wherein the compound is a cabozantinib metabolite selected from:

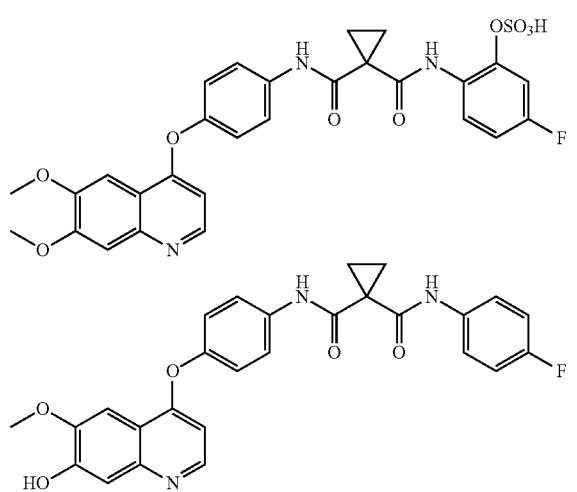

Another aspect of the invention is a method of screening for a modulator of a kinase, said kinase selected from c-Met, KDR, RET, c-Kit, flt-3, and flt-4, the method comprising combining a compound and at least one candidate agent and determining the effect of the candidate agent on the activity of said kinase, wherein the compound is a cabozantinib metabolite selected from:

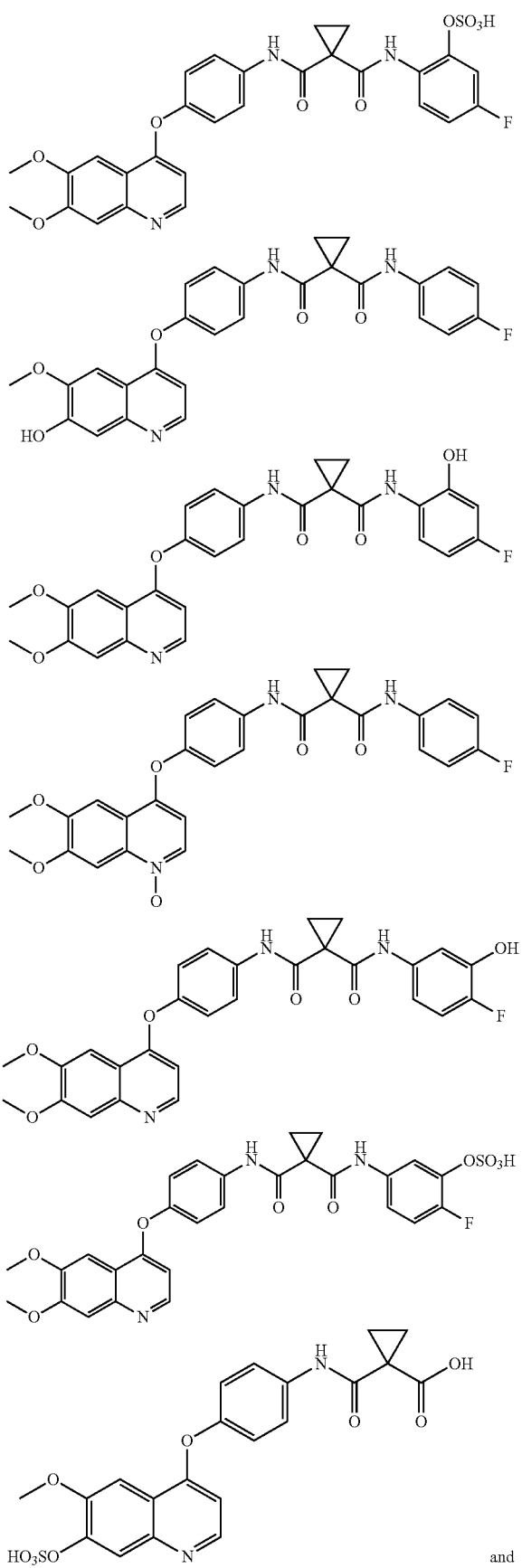

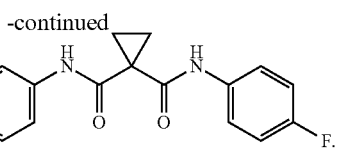

Isolated metabolites as described above that exhibit inhibitory activity against c-MET or other kinases can be formulated into suitable dosage forms for administration to humans or other mammals. In some embodiments, the metabolites may exhibit favorable toxicological profiles in comparison to conventional therapy or therapy with cabozantinib.

As inhibitors of c-MET, in some embodiments, the metabolites are used to treat cancer. "Cancer" includes tumor types such as tumor types including breast, colon, renal, lung, squamous cell myeloid leukemia, hemangiomas, melanomas, astrocytomas, and glioblastomas as well as other cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia, renal cell carcinoma), bladder and urethra (squamous cell carcinoma, transitional cell carcinoma, adenocarcinoma), prostate (adenocarcinoma, sarcoma, small cell carcinoma of the prostate), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; as well as cancers of the thyroid including medullary thyroid cancer. Thus, the term "cancerous cell," as provided herein, includes a cell afflicted by any one of the above-identified conditions.

In one embodiment, the cancer is selected from ovarian cancer, prostate cancer, lung cancer, medullary thyroid cancer, liver cancer, gastrointestinal cancer, pancreatic cancer, bone cancer, hematologic cancer, skin cancer, kidney cancer, breast cancer, colon cancer, and fallopian tube cancer.

In another embodiment, the disease or disorder is ovarian cancer.

In another embodiment, the disease or disorder is prostate cancer.

In another embodiment, the disease or disorder is lung cancer.

In another embodiment, the disease or disorder is medullary thyroid cancer.

In another embodiment, the disease or disorder is liver cancer.

In another embodiment, the disease or disorder is gastrointestinal cancer.

In another embodiment, the disease or disorder is pancreatic cancer.

In another embodiment, the disease or disorder is bone cancer.

In another embodiment, the disease or disorder is hematologic cancer.

In another embodiment, the disease or disorder is skin cancer.

In another embodiment, the disease or disorder is kidney cancer.

In another embodiment, the disease or disorder is breast cancer.

In another embodiment, the disease or disorder is colon cancer.

In another embodiment, the disease or disorder is fallopian cancer.

In another embodiment, the disease or disorder is liver cancer, wherein the liver cancer is hepatocellular carcinoma, cholangiocarcinoma, hepatoblastoma, angiosarcoma, hepatocellular adenoma, or hemagioma.

In another embodiment, the disease or disorder is gastrointestinal cancer, wherein the gastrointestinal cancer is cancer of the esophagous which is squamous cell carcinoma, adenocarcinoma, or leiomyosarcoma; cancer of the stomach which is carcinoma, or lymphoma; cancer of the pancreas, which is ductal adenocarcinoma, insulinoma, gucagonoma, gastrinoma, carcinoid tumors, or vipoma; cancer of the small bowel, which is adenocarcinoma, lymphoma, carcinoid tumors, Karposi's sarcoma, leiomyoma, hemagioma, lipoma, or cancer of the large bowel, which is adenocarcinoma, tubular adenoma, villous adenoma, hamartoma, or leiomyoma.

In another embodiment, the disease or disorder is cancer of the pancreas, wherein the cancer of the pancreas is ductal adenocarcinoma, insulinoma, gucagonoma, gastrinoma, carcinoid tumors, or vipoma.

In another embodiment, the disease or disorder is bone cancer, wherein the bone cancer is osteosarcoma, fibrosarcoma, malignant fibrous histiocytoma, chondrosarcoma, Ewing's sarcoma, malignant reticulum cell sarcoma, multiple myeloma, malignant giant cell tumor chordoma, osteocartiliginous exostoses, chondroblastoma, chondromyxofibroma, or osteoid osteoma.

In another embodiment, the disease or disorder is hematologic cancer, wherein the hematologic cancer is myeloid leukemia, acute lymphoblastic leukemia, chronic lymphocytic leukemia, myeloproliferative diseases, multiple myeloma, or myelodysplastic syndrome.

In another embodiment, the disease or disorder is skin cancer, wherein the skin cancer is malignant melanoma, basal cell carcinoma, squamous cell carcinoma, or Karposi's sarcoma.

In another embodiment, the disease or disorder is a renal tumor or renal cell carcinoma.

In another embodiment, the disease or disorder is breast cancer.

In another embodiment, the disease or disorder is a colon cancer tumor.

In another embodiment, the disease or disorder is fallopian tube carcinoma.

Alternatively, or additionally, the metabolites are administered to subjects or test animals not having any of the above mentioned disease states for the purpose of studying non-pharmacological effects, such as side effects, toxicity, metabolism, uptake, bioavailability, and routes of excretion.

In various embodiments, the metabolites are administered by any suitable route including oral, rectal, intranasal, intrapulmonary (e.g., by inhalation), or parenteral (e.g. intradermal, transdermal, subcutaneous, intramuscular, or intravenous) routes. Oral administration is preferred in some embodiments, and the dosage can be given with or without food, i.e. in the fasting or non-fasting state. Non-limiting examples of dosage forms include uncoated or coated tablets, capsules, powders, granules, suppositories, solutions, ointments, creams, and sprays.

Formulations of the invention suitable for oral administration are prepared as discrete units, such as capsules, cachets, or tablets, each containing a predetermined amount of the active ingredient; as a powder or granules; as solution or a suspension in an aqueous liquid or a non-aqueous liquid; or as an oil-in-water liquid emulsion; or a water-in-oil liquid emulsion. The active ingredient may also be presented as a bolus, electuary, or paste.

A tablet is made by compression or molding, optionally with one or more accessory ingredients. Compressed tablets may be prepared by compressing in a suitable machine the active ingredient in a free-flowing form, such as a powder or granules, optionally mixed with a binder, lubricant, inert diluent, preservative, surface active, or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. In one embodiment, acid hydrolysis of the medicament is obviated by use of an enteric coating.

An enteric coating is a means of protecting a compound of the invention in order to avoid exposing a portion of the gastrointestinal tract, typically the upper gastrointestinal tract, in particular the stomach and esophagus, to the compound of this invention. In this way, gastric mucosal tissue is protected against rates of exposure to a compound of the invention which produce adverse effects such as nausea; and, alternatively, a compound of the invention is protected from conditions present in one or more portions of the gastrointestinal tract, typically the upper gastrointestinal tract.

Formulations suitable for topical administration in the mouth include lozenges comprising the active ingredient in a flavored basis, usually sucrose and acacia or tragacanth; pastilles comprising the active ingredient in an inert basis such as gelatin and glycerin or sucrose and acacia; and mouthwashes comprising the active ingredient in a suitable liquid carrier.

Formulations for rectal administration may be presented as a suppository with a suitable base comprising, for example, cocoa butter or a salicylate.

While it is possible for the active ingredients to be administered alone, it may be preferable to present them as pharmaceutical formulations. The formulations, both for veterinary and for human use, comprise at least one active ingredient, as defined above, together with one or more acceptable carriers and optionally comprising other therapeutic ingredients. The carrier(s) must be "acceptable" in that they are compatible with the other ingredients of the formulation and physiologically innocuous to the recipient thereof.

In various embodiments the compounds are formulated in a carrier system. Such systems are known and include binders, fillers, preservatives, disintegrants, flow regulators, plasticizers, wetting agents, emulsifiers, dispersants, lubricants, solvents, release slowing agents (including enteric coatings), antioxidants, and propellant gases. Especially when formulated for administration to humans, the active agents are preferably combined with at least one pharmaceutically acceptable carrier. Such carriers are known and include, without limitation, cellulose derivatives, polyethylene glycol, and N-vinylpyrrolidone polymers. The administration forms comprise a therapeutically effective amount of the compounds, which make up from 0.1% to about 90% by weight of the dosage form.

The compounds of this invention are formulated with conventional carriers and excipients, which are selected in accord with ordinary practice. Tablets will contain excipients, glidants, fillers, binders, and the like. Aqueous formulations are prepared in sterile form and, when intended for delivery by other than oral administration, generally will be isotonic. All formulations will optionally contain excipients, such as those set forth in the "Handbook of Pharmaceutical Excipients" (1986). Excipients include ascorbic acid and other antioxidants, chelating agents such as EDTA, carbohydrates such as dextrin, hydroxyalkylcellulose, hydroxyalkylmethylcellulose, stearic acid, and the like.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

In a particular embodiment, the invention provides a pharmaceutical composition comprising a cabozantinib metabolite which is a compound selected from:

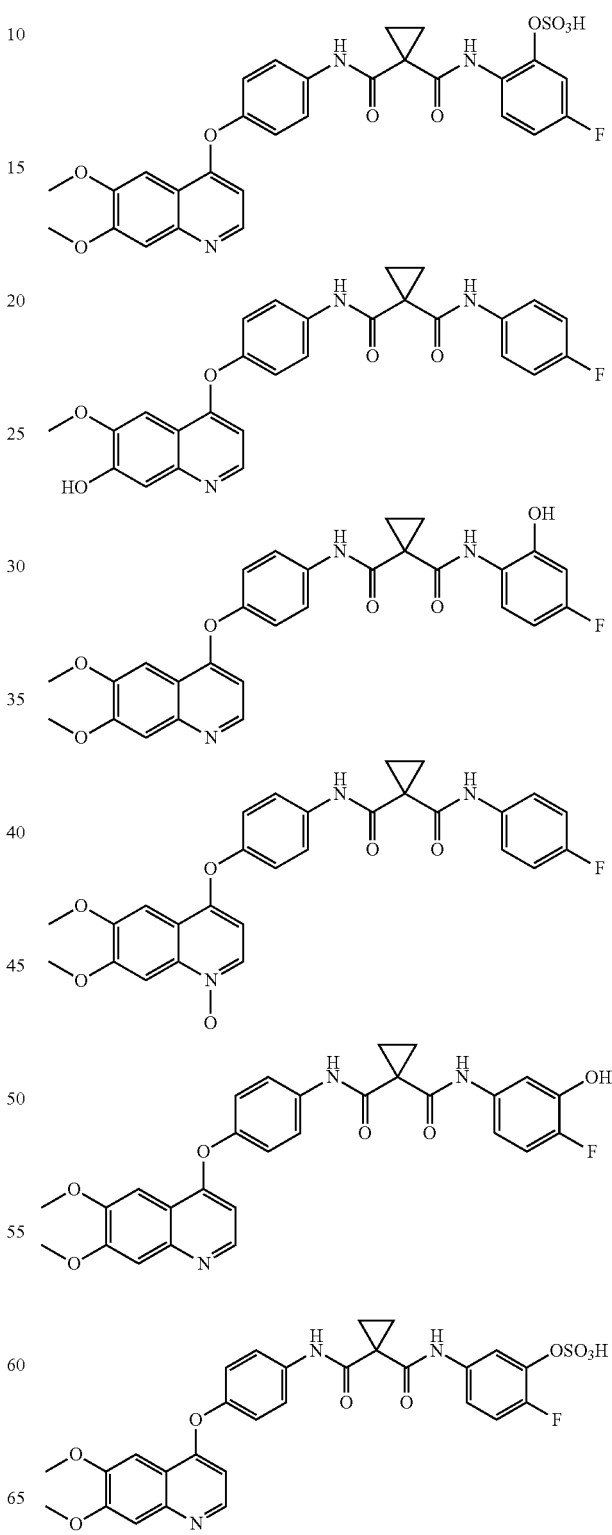

-continued

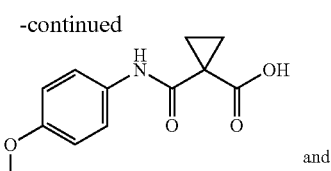
and
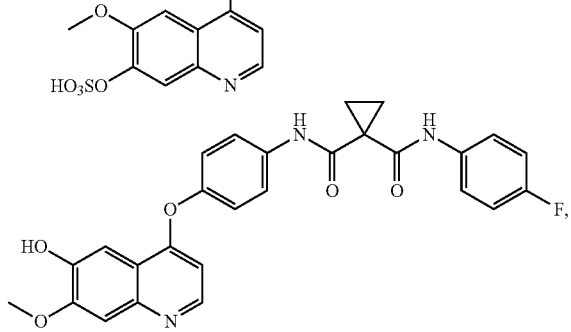

or a pharmaceutically acceptable salt thereof, and at least one pharmaceutically acceptable carrier.

The compounds disclosed herein can be made according to methods available to the skilled practitioner. For example, as depicted in Scheme 2, peptide chemistry can be used to make the phenols C-1 and C-2 from the corresponding amines and carboxylic acids. A variety of processes and reagents are available for achieving such transformations and are described, for instance, in Tetrahedron 61 (2005) 10827-10852. A representative example is depicted in Scheme 2, wherein the activating agent is thionyl chloride, oxalyl chloride, or the like. The corresponding acid chloride reacts with compound A or B, respectively, to provide phenol C-1 or C-2. Subsequent reaction of phenol C-1 or C-2 with a sulfating agent, such as chlorosulfonic acid or sulfur trioxide-trimethylamine complex, in the presence of a base, such as triethylamine, alkali metal hydroxide or the like, can provide the corresponding hydrogen sulfate 2b or 2a, respectively.

Scheme 2

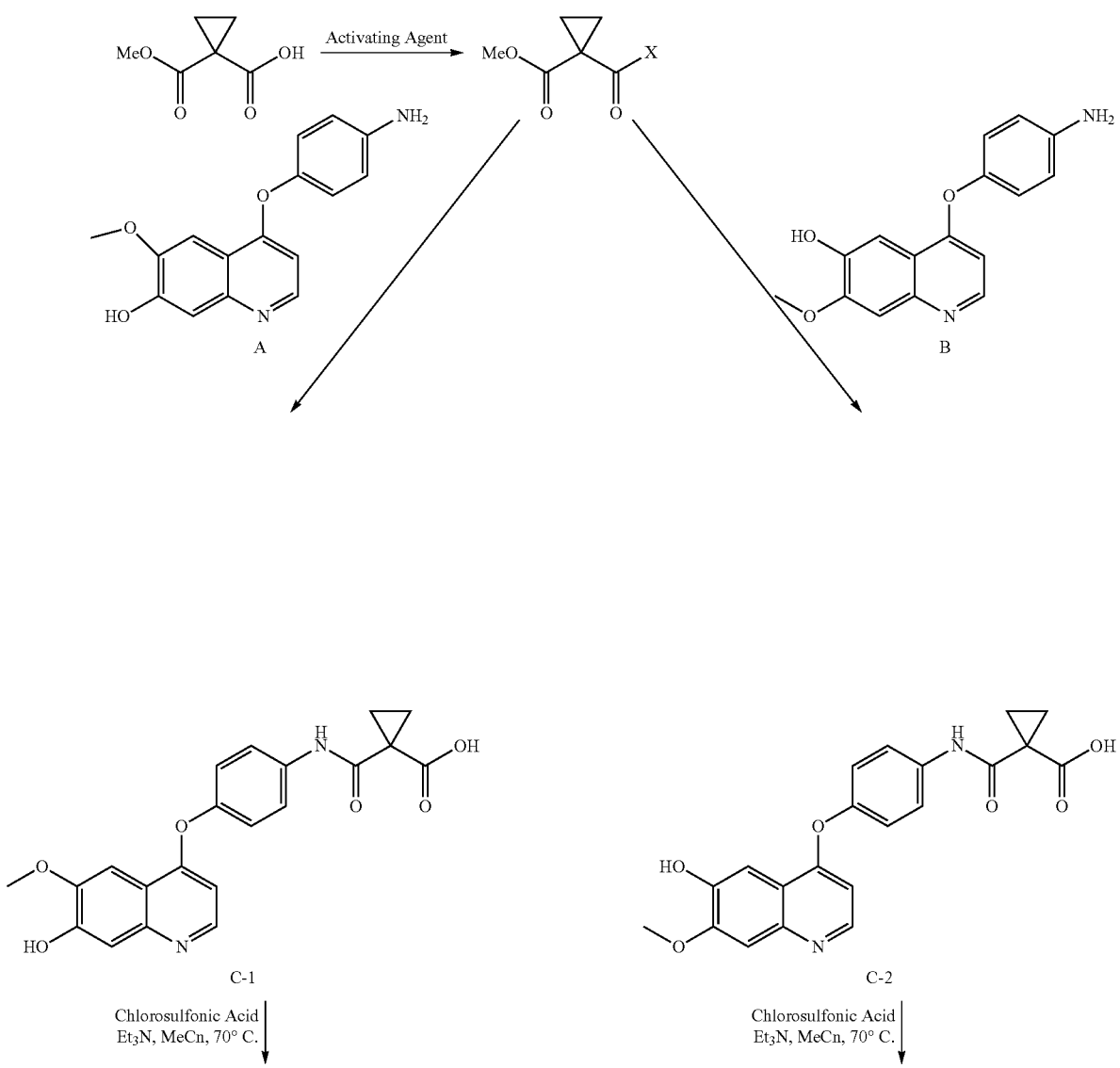

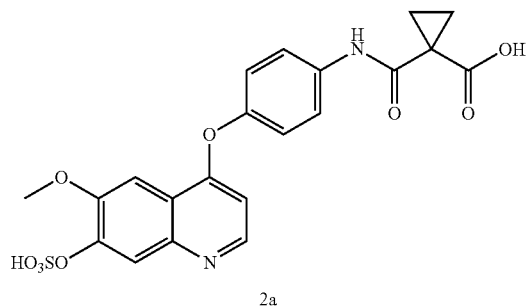

2a

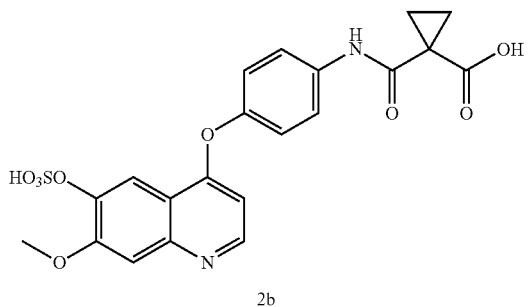

2b

Compound A was prepared according to Scheme 3. Benzylation of A-1 using a benzyl halide or the like provides benzyl-protected A-2. Nitration of A-2 using a mixture of nitric acid and sulfuric acid provides A-3. Reduction of nitro group in A-3 to the amine A-4, may be accomplished using standard nitro reduction conditions, such as iron and ammonium acetate. Cyclization of A-4 with ethyl formate and an alkoxide such as sodium methoxide provides the A-5. Conversion of A-5 to the corresponding chloride using phosphorous oxychloride provides A-6. Reaction of A-6 with 4-amino phenol provides A-7, which is deprotected with methane sulfonic acid to provide compound A.

Scheme 3

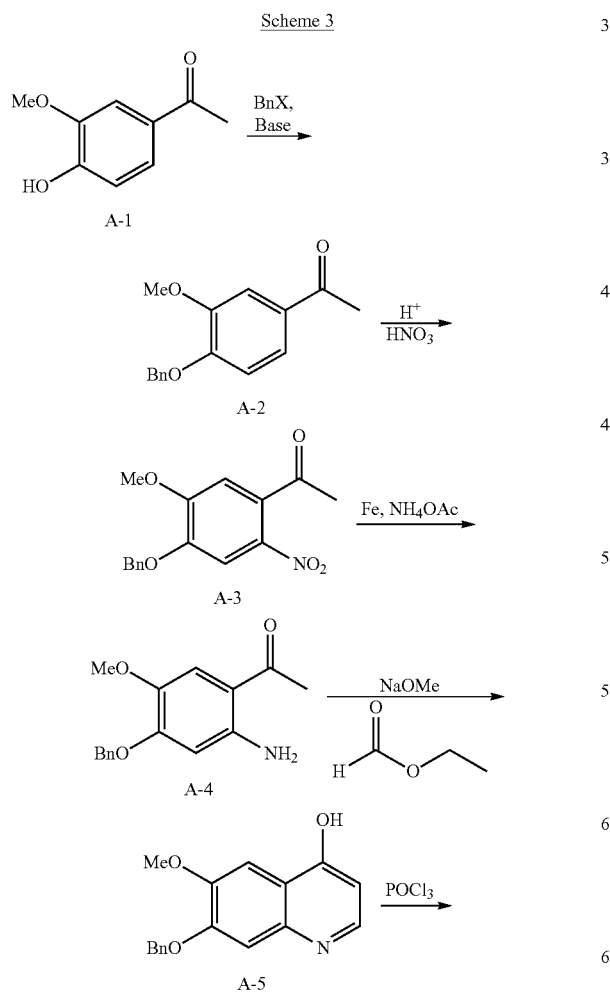

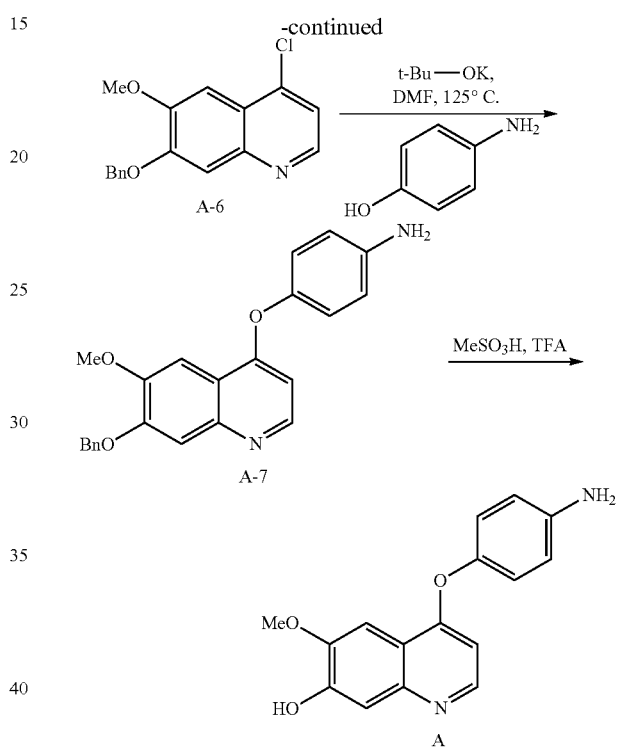

Similarly, compound B was prepared according to Scheme 4. Demethylation of B-1 provides B-2. Benzylation of B-2 using a benzyl halide BnX, wherein X is Br Cl or I, or the like provides benzyl-protected B-3. Nitration of B-3 using a mixture of nitric acid and sulfuric acid provides B-4. Reduction of nitro group in B-4 to the amine B-5, may be accomplished using standard nitro reduction conditions, such as iron and ammonium acetate. Cyclization of B-5 with ethyl formate and an alkoxide such as sodium methoxide provides the B-6. Conversion of B-6 to the corresponding chloride using phosphorous oxychloride provides B-7. Reaction of B-7 with 4-amino phenol provides B-8, which was deprotected with methane sulfonic acid to provide compound B.

Scheme 4

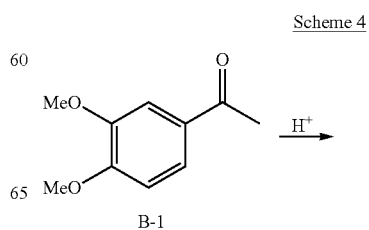

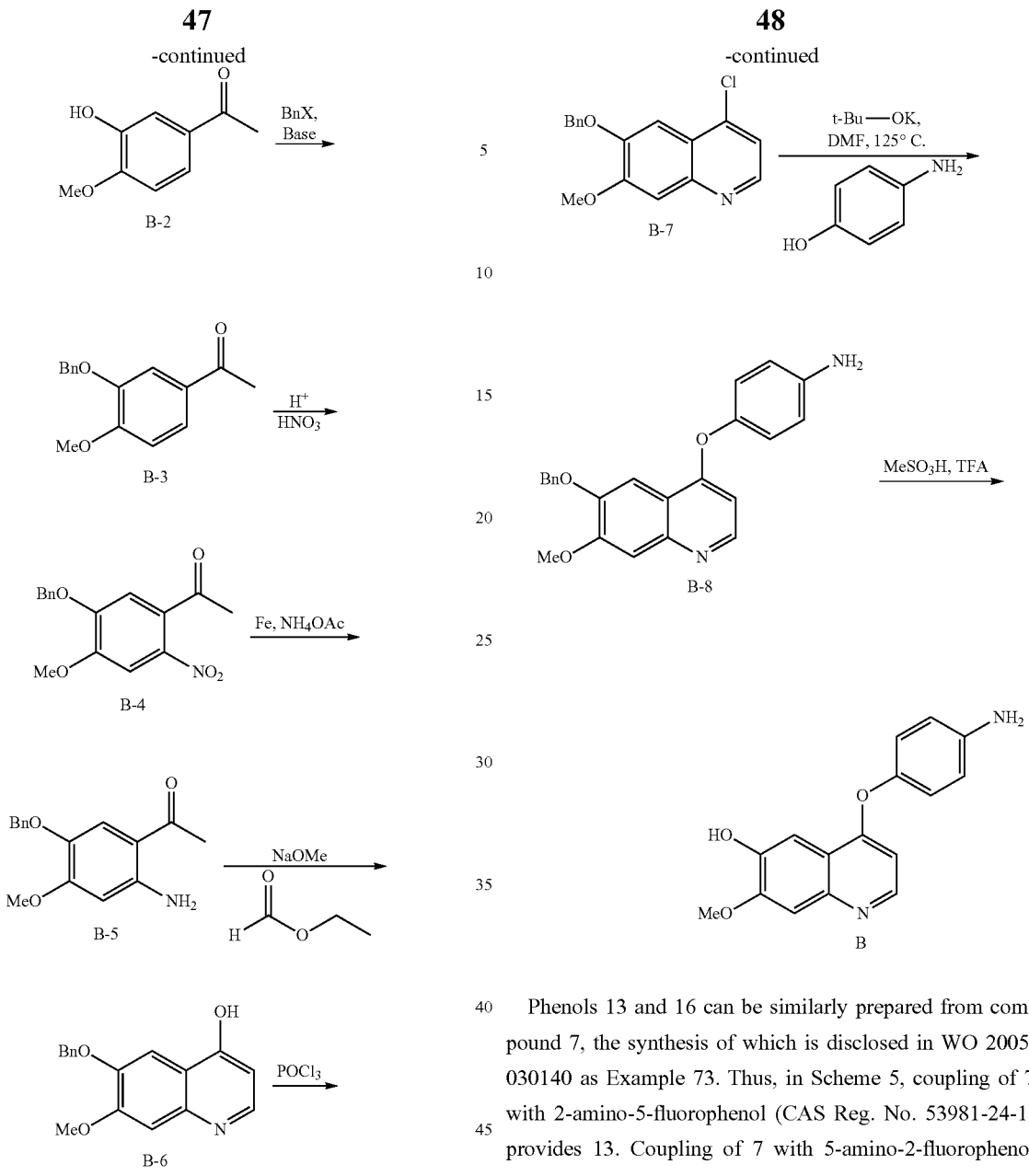
Phenols 13 and 16 can be similarly prepared from compound 7, the synthesis of which is disclosed in WO 2005/030140 as Example 73. Thus, in Scheme 5, coupling of 7 with 2-amino-5-fluorophenol (CAS Reg. No. 53981-24-1) provides 13. Coupling of 7 with 5-amino-2-fluorophenol (CAS Reg. No. 100367-48-4) provides 16.
Scheme 5
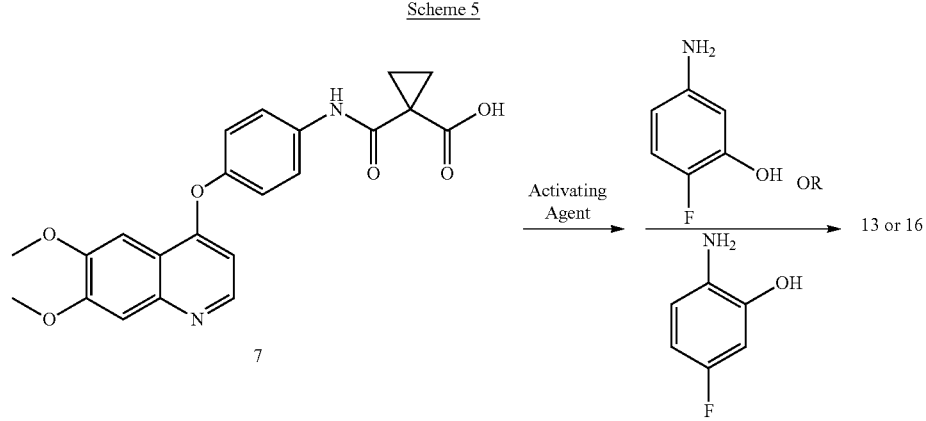

Phenols 13 and 16 can be readily converted to the corresponding sulfates 9, and 12 depicted in Scheme 1 using, for example, a sulfating agent, such as sulfur trioxide trimethyl amine complex, in the presence of a strong hydroxide, such as potassium hydroxide, sodium hydroxide, or the like, or using chlorosulfonic acid in the presence of an amine base such as triethylamine.

The phenols 15a and 15b can be prepared by employing the similar method that is disclosed in WO 2005/030140 for the preparation of Example 43. Thus, in Scheme 6, coupling of phenol C (Example 38 in WO 2005/030140) with triflate D (Example 33 in WO 2005/030140), or chloride A-6 (Example 32 in WO 2005/030140) provides E, which is then deprotected under Pd-catalyzed hydrogenolysis condition to yield compound 15. Similarly, reaction of phenol C with triflate F or chloride B-7 provides G, which is subjected to O-benzyl deprotection to provide compound 15b.

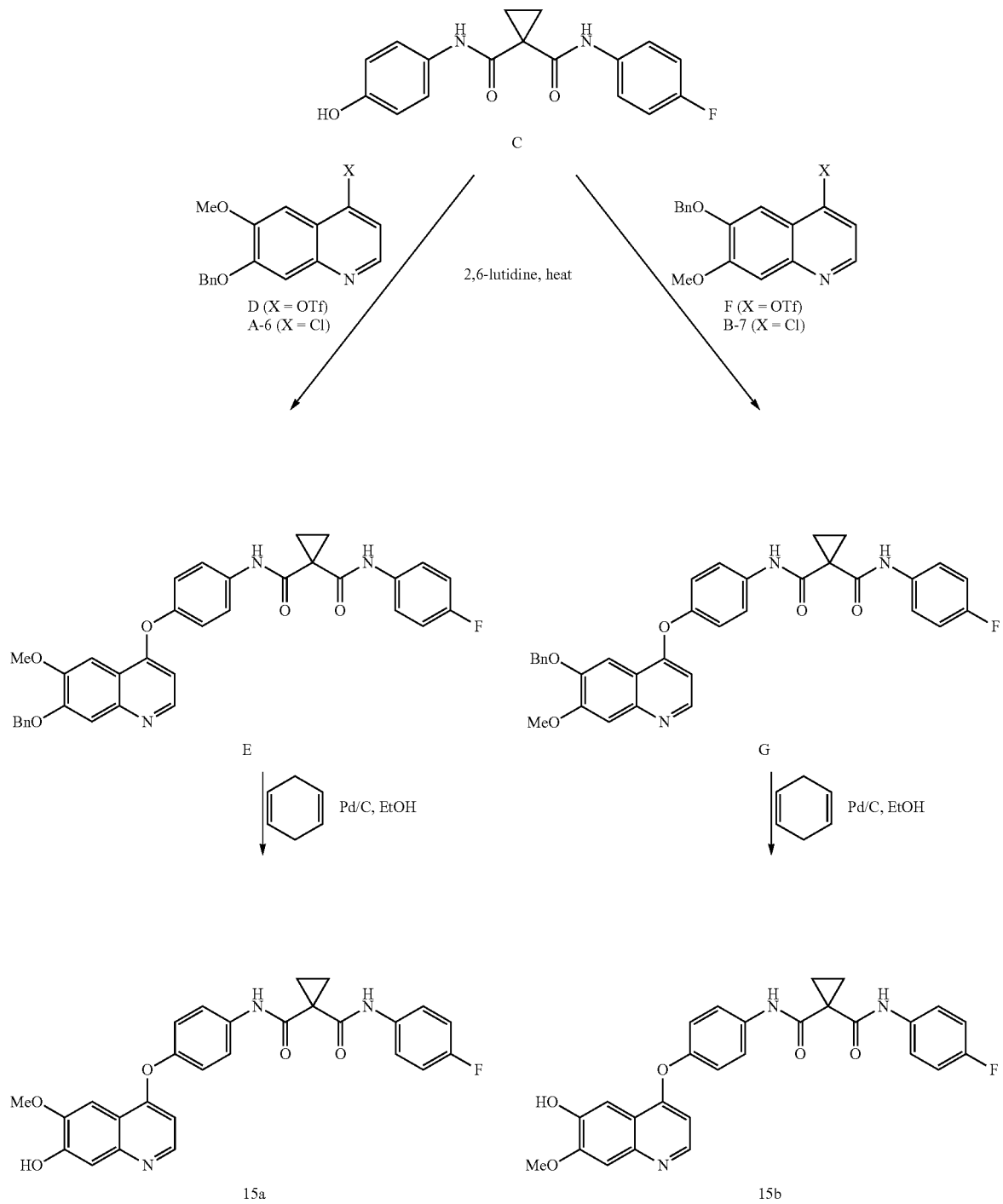

The N-oxide 19 can be prepared by the reaction of cabozantinib with an oxidizing agent, such as, for example a peroxide, a peracid, or the like. In one embodiment, the oxidizing agent is sodium perborate tetrahydrate.

The following non-limiting examples are meant to illustrate the invention.

Examples

Identification of Cabozantinib Metabolites

The objective of this study was to profile and identify metabolites of cabozantinib in human plasma, urine, and feces. The plasma, urine and fecal samples were collected from a mass balance study of cabozantinib following a single 175 mg oral administration of cabozantinib (L-malate salt) containing [$^{14}$C] cabozantinib (100 µCi) in healthy male subjects.

Study Design and Plasma, Urine, and Feces Sampling

Eight male subjects participated in the study, and each subject received a single oral dose of 175 mg of cabozantinib (L-malate salt) containing [$^{14}$C]-cabozantinib (100 µCi). The plasma, urine, and fecal samples were collected from the 8 subjects for the metabolite profiling.

Plasma samples were collected at pre-dose, 0.5, 1, 2, 3, 4, 5, 8, 14, 24, 72, 168, 336, 504 and 648 hours post-dose; urine samples were collected at pre-dose, 0-8 hours, 8-24 hours, at 24-hour intervals to 480 hours post-dose, and at greater than 48-hour intervals from 504 to 1152 hours post-dose; and feces samples were collected at pre-dose, at 24-hour intervals to 480 hours post-dose, and at greater than 48-hour intervals from 504 to 1152 hours post-dose. All samples were shipped to QPS LLC (Newark, Del.) and stored at −70° C. HPLC/tandem MS coupled with a radio flow-through detector (RFD) was used for metabolite profiling and identification for samples with sufficient levels of radioactivity.

HPLC fraction collection followed by counting with TopCount NXT™ was used for radioquantitation of plasma samples with sufficient levels of radioactivity. Three (3) HPLC methods were used in this study to separate cabozantinib and its metabolites. HPLC Method 1 was used for the analysis of pooled urine and fecal samples and individual plasma samples from different time points. HPLC Method 2 was used for the analysis of plasma samples from a drug-drug interaction study to search for possible metabolites that may co-elute with cabozantinib sulfate. HPLC Method 3 was used for pooled plasma samples.

Selected samples for plasma, urine, and feces from 6 subjects were analyzed for cabozantinib and metabolites and reported.

Samples from 2 subjects were used for the investigation study.

Test Article

The test article for this study was a mixture of [$^{14}$C] cabozantinib and cabozantinib. The asterisk indicates the position of the [$^{14}$C] label. [$^{14}$C] labeled cabozantinib was prepared as provided in WO 2005/030140, except that [$^{14}$C] labeled 4-amino phenol was used instead of unlabeled 4-amino phenol. [$^{14}$C] labeled 4-amino phenol is commercially available as the hydrochloride salt, for instance, from Hartmann Analytic, American Radiolabeled Chemicals, or Fisher Scientific.

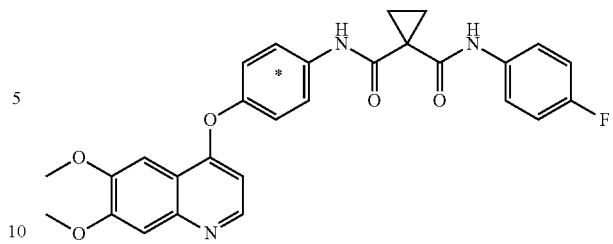

General Chemicals and Reference Standards

Formic acid and ammonium acetate were obtained from Sigma-Aldrich Chemical Co. (St. Louis, Mo.). Acetonitrile (B & J brand, carbonyl free, for applications sensitive to trace aldehyde and ketone), water (B & J brand, for GC, HPLC and spectrophotometry), and methanol (HPLC grade) were purchased from Fisher Scientific (Pittsburgh, Pa.). Type I water was generated using an Elgastat UHQ PS water purification system. Non-radiolabeled metabolite standards (fluoroaniline cleavage product, cabozantinib sulfate, and cabozantinib N-oxide) were provided by Exelixis, Inc.

Biological Sample Collection

The plasma, urine, and fecal samples were collected from a mass balance study of cabozantinib following a single 175 mg oral administration of cabozantinib (L-malate salt) containing [$^{14}$C] cabozantinib (100 µCi) in healthy male subjects. Samples were shipped from Celerion (Lincoln, Nebr.) to QPS LLC (Newark, Del.) on dry ice and were stored at −70° C. until analysis. Samples from 6 subjects were used for metabolite profiling, identification, and radio-quantitation. Plasma samples from 2 subjects were only used in a bridging study as part of investigation of co-eluting metabolites.

Sample Preparation and Radioactive Recovery for Human Plasma

For metabolite profiling, identification, and radio-quantitation, individual radiolabeled plasma samples collected at 0.5, 1, 2, 3, 4, 5, 8, 14, 24, 72, 168, and 336 hours post-dose were processed and analyzed for 6 subjects. For the investigation of co-eluting metabolites, nonradiolabeled plasma samples of six subjects were pooled, processed, and analyzed for pre-dose, 1-7, 8-96, and 120-336 hours post-dose. To bridge the metabolite data from non-radiolabeled to radiolabeled plasma samples from the human mass balance study, [$^{14}$C] plasma samples from 0-168 hours post-dose for each of the six subjects were also pooled using the Hamilton pooling method, processed, and analyzed by radio-quantitation. [$^{14}$C] Plasma samples from 1-168 hours post-dose for two subjects were pooled (equal volume), processed, and analyzed.

Initial Method for Plasma Extraction and Recovery

Two plasma samples from a subject (4 and 72 hours post-dose) were used for initial extraction and recovery determination. The total radioactivity for each plasma sample in mass balance study was provided by Exelixis, Inc., and was defined as 100%. After the samples were thawed under a biological hood, two 0.5 mL aliquots of each plasma sample were added to 3 volumes (1.5 mL) of MeOH:ACN (20:80, v/v) and vortexed (5 min). The mixtures were centrifuged at 2000 rpm for 10 minutes, and the supernatants were transferred to clean tubes. The pellets were extracted with two additional 3 volumes of MeOH:CAN (20:80, v/v). The mixtures were centrifuged, and the supernatants were combined. Aliquots were analyzed by a 2900 TR liquid scintillation counter (LSC) (Packard Instruments, Meridian, Conn.). The extraction recovery was calculated as the following:

Extraction Recovery (%)=(DPM in supernatant/DPM in plasma sample)×100

The supernatants from the extraction were evaporated to dryness under a stream of nitrogen in an ambient water bath. The residues were then reconstituted in 0.35-0.5 mL of MeOH:ACN:water (10:20:70, v/v/v). The reconstituted samples were centrifuged at 15,000 rpm for 10 minutes and aliquots were analyzed by LSC for reconstitution recovery.

Reconstitution Recovery (%)=(DPM in reconstitution solution/DPM in supernatant)×100

Plasma Sample Preparation

Radiolabeled and non-radiolabeled plasma samples were extracted employing the same method, using 1.0-2 mL plasma samples, depending on the volume available and radioactivity level of the samples. The supernatants were evaporated to dryness under a stream of nitrogen in an ambient water bath, and the residues were reconstituted in 0.35-0.5 mL of MeOH:ACN:water (10:20:70, v/v/v). The reconstituted samples were centrifuged at 15,000 rpm for 10 minutes. Aliquots of the supernatants were injected onto the HPLC system for analysis.

Sample Preparation and Radioactive Recovery for Human Urine

Pooled urine samples from a subject (0-72, 168-192, and 312-336 hours post dose) were lyophilized in triplicate (each 4 mL), and the residues were reconstituted in 1 mL of water:ACN:FA (80:20:0.1, v/v/v). The radioactivity in pooled urine and reconstituted solution was counted using LSC, and the reconstitution recovery calculated. For metabolite profiling, identification, and radio-quantitation, pre-dose and 3 pooled urine samples (0-72 hours, 168-192 hours, and 312-336 hours post-dose) from each of the six subjects were analyzed. Each pooled urine sample was lyophilized, the residue was reconstituted in water:ACN:FA (80:20:0.1, v/v/v), and the reconstituted sample was centrifuged at 15,000 rpm for 10 min before analysis.

Sample Preparation and Radioactive Recovery for Human Urine

To evaluate the extraction recovery of fecal samples, two fecal homogenate samples from a subject were thawed under a biological hood. Approximately 5.5-6 g fecal homogenate was accurately weighed out for the extraction. Fifteen mL ACN:MeOH (80:20) was added to the fecal homogenates. The mixtures were vortexed for 3 minutes and centrifuged at 3000 rpm for 10 minutes. The supernatants were transferred to clean tubes. The extraction procedure was repeated two more times. The supernatants from all three extractions were combined. The radioactivity in the combined supernatants was determined by LSC. The extraction recovery was calculated using the following formula:

Extraction Recovery (%)=(DPM in supernatant/DPM in fecal homogenate)×100

The supernatant was concentrated under a nitrogen stream at ambient temperature, and the residues were reconstituted in MeOH:ACN:water (10:20:70). Aliquots of reconstitution solution were counted with LSC for reconstitution recovery.

Reconstitution Recovery (%)=(DPM in reconstitution solution/DPM in supernatant)×100

Overall Recovery (%)=Extraction Recovery (%)× Reconstitution Recovery (%)/100

For metabolite profiling, identification, and radio-quantitation, pre-dose and 3 pooled fecal samples (0-72, 168-192, and 312-336 hours post-dose) from each of the six subjects were extracted using the same procedures for extraction recovery. The supernatants were dried under a nitrogen stream, and the residues were reconstituted in water:ACN:FA (80:20:0.1, v/v/v). The reconstituted samples were centrifuged at 15,000 rpm for 10 min before analysis.

HPLC Column Recovery

HPLC column recovery was carried out to demonstrate that all radioactive components were effectively eluted from the column using HPLC Method 1. Aliquots of urine samples (Subject 1042, 24-48 hours post-dose) were injected onto the HPLC system with or without a column, and the eluents from 0-30 minutes were collected into clean 50 mL centrifuge tubes. The weights of eluent from each injection were obtained after collection, and duplicate aliquots (1 mL) were counted using LSC. The average value of the counts was used to calculate the total radioactivity contained in the collected eluent with or without a column installed.

Column Recovery (%)=(DPM in eluent with column/DPM in eluent without column)×100

HPLC Method 3 was used for pooled plasma only, and the column recovery was not performed due to limited sample volume available.

HPLC/MS/RFD and HPLC Radio-Analysis Systems

The system for metabolite profiling and identification (HPLC/MS/RFD) consisted of a HTC PAL autosampler, a Surveyor HPLC pump, a LTQ linear ion trap mass spectrometer, and a β-RAM Model 3 RFD. The data obtained by mass spectrometry and RFD were processed by Xcalibur and Laura Lite 3 software, respectively. The HPLC eluent was split between the RFD and mass spectrometer with a ratio of 3 to 1. The following are the summary of the conditions for HPLC, mass spectrometer, and RFD.

HPLC/MS/RFD Method 1

| HPLC | Surveyor HPLC pump | | |
|---|---|---|---|
| Column Type | Phenominex Synergi Polar RP, 4.6 × 250 mm, 4 μm | | |
| Mobile Phases | A: H$_2$O with 0.1% FA B: ACN with 0.1% FA | | |
| | Time (min) | A % | B % |
| Gradient Program | 0 | 80 | 20 |
| | 2 | 80 | 20 |
| | 22 | 30 | 70 |
| | 23 | 5 | 95 |
| | 27 | 5 | 95 |
| | 28 | 80 | 20 |
| | 34 | 80 | 20 |
| Flow Rate | 800 μL/minutes | | |
| Analysis Time | 34 minutes | | |
| Mass Spectrometry: | Thermo Finnigan LTQ Linear Ion Trap | | |
| Sheath gas flow rate | 50 unit | | |
| Auxiliary gas flow rate | 20 unit | | |
| Sweep gas flow rate | 10 unit | | |
| Ion spray voltage | 5 kV for ESI+; 4.3 kV for ESI− | | |
| Capillary temperature | 300° C. | | |
| Capillary voltage | 22 V for ESI+; −9 V for ESI− | | |
| Tube lens voltage | 80 V for ESI+; −96 V for ESI− | | |
| Ionization mode | ESP−, ESI− | | |
| Radio Flow-through Detector: | β-RAM Model 3 | | |
| Radionuclide | $^{14}$C | | |
| Cell Volume | 400 μL | | |
| Scintillation Cocktail | Ultima-Flo M, Perkin Elmer | | |
| Cocktail/HPLC flow ratio | 3:1 | | |

HPLC/MS Method 2

| HPLC | Surveyor HPLC pump | | |
|---|---|---|---|
| Column Type | Phenominex Synergi Polar RP, 4.6 × 250 mm, 4 μm | | |
| Mobile Phases | A: H$_2$O with 0.1% FA | | |
| | B: ACN with 0.1% FA | | |
| | Time (min) | A % | B % |
| Gradient Program | 0 | 80 | 20 |
| | 2 | 80 | 20 |
| | 40 | 35 | 65 |
| | 42 | 5 | 95 |
| | 47 | 5 | 95 |
| | 48 | 80 | 20 |
| | 55 | 80 | 20 |
| Flow Rate | 800 μL/minutes | | |
| Analysis Time | 55 minutes | | |
| Mass Spectrometry: | Thermo Finnigan LTQ Linear Ion Trap | | |
| Sheath gas flow rate | 50 unit | | |
| Auxiliary gas flow rate | 20 unit | | |
| Sweep gas flow rate | 10 unit | | |
| Ion spray voltage | 5 kV | | |
| Capillary temperature | 300° C. | | |
| Capillary voltage | 22 V | | |
| Tube lens voltage | 80 V | | |
| Ionization mode | ESI+ | | |

HPLC/MS Method 3

| HPLC | Surveyor HPLC pump | | |
|---|---|---|---|
| Column Type | Waters Xbridge phenyl, 4.6 × 150 mm, 3.5 μm | | |
| Mobile Phases | A: H$_2$O with 0.1% FA | | |
| | B: ACN with 0.15% FA | | |
| | Time (min) | A % | B % |
| Gradient Program | 0 | 80 | 20 |
| | 2 | 80 | 20 |
| | 40 | 30 | 70 |
| | 42 | 5 | 95 |
| | 47 | 5 | 95 |
| | 48 | 80 | 20 |
| | 55 | 80 | 20 |
| Flow Rate | 800 μL/minutes | | |
| Analysis Time | 55 minutes | | |
| Mass Spectrometry: | Thermo Finnigan LTQ Linear Ion Trap | | |
| Sheath gas flow rate | 50 unit | | |
| Auxiliary gas flow rate | 20 unit | | |
| Sweep gas flow rate | 10 unit | | |
| Ion spray voltage | 5 kV | | |
| Capillary temperature | 300° C. | | |
| Capillary voltage | 22 V | | |
| Tube lens voltage | 80 V | | |
| Ionization mode | ESI+ | | |

The HPLC-MS system for high resolution MS consisted of a Michrom Bioresources Paradigm MS4B HPLC and a Thermo LTQ Orbitrap Discovery mass spectrometer. Chromatographic conditions and the ion source parameters were the same as HPLC method 1 for the LTQ system. Data were acquired with a resolution of 30000 in centroid mode.

An HPLC/TopCount NXT™ system was used for the radio-quantitation of plasma samples. The system consisted of an HTC PAL autosampler, two Shimadzu HPLC pumps, and a Foxy Jr. Fraction Collector (Isco, Lincoln, Nebr.). HPLC fractions collected in a LumaPlate™ 96-well plate were dried using an EZ-2$_{plus}$ Personal Evaporator (Genevac, Valley Cottage, N.Y.), and the dried samples were counted by TopCount NXT™ Microplate Scintillation & Luminescence Counter (PerkinElmer®). The data were processed using ProFSA (PerkinElmer®) software. The HPLC methods were the same as described above.

Metabolite Identification

Metabolites that represented greater than 5% of the total radioactivity or 5% of total AUC in the matrix were identified according to the following process. Mass spectra (MS, MS/MS, and MS/MS/MS) of cabozantinib and its metabolite standards, provided by the Exelixis, Inc., were acquired on an ion trap mass spectrometer. Major fragment patterns were proposed. Identification of these metabolites was confirmed by matching mass spectra (MS and MS/MS) and retention times with authentic reference standards. For other unknown metabolites, molecular ions were searched on LC/MS chromatograms operating in full scan positive as well as negative ionization modes at the same retention times as those found on LC-radio chromatogram. Product ion mass spectra and high resolution mass spectra were then acquired for the corresponding molecular ions. Putative metabolite structures were proposed based on the analysis of their mass fragment patterns.

Quantitation of cabozantinib and its Metabolites

Quantitation of cabozantinib and its metabolites in pooled or individual samples from each matrix at different time points or time intervals was based on integration of the corresponding peaks found on their radio-chromatograms. For plasma samples, percent of total radioactivity in the sample for each peak at each time point was calculated and converted to ng/mL.

For quantification of cabozantinib and its metabolites in plasma:

ng/mL=(% of the total radioactivity)×(total ng equivalent/mL for the time point)/100

The values of total ng equivalent/mL were obtained from the results of the human mass balance study.

For the pooled urine samples, percent of total radioactivity in the pooled sample for each peak was calculated as the % of total non-parent in the pooled samples:

% of total non-parent in the pooled samples=(total radioactivity of the peak/total radioactivity of the non-parent peaks)×100

For the pooled fecal samples, percent of total radioactivity in the pooled sample for each peak was calculated as the percent of total non-parent plus parent in the pooled samples:

% of total non-parent plus parent in the pooled samples=(total radioactivity of the peak/total radioactivity of the parent and non-parent peaks)×100

The percent of total radioactivity in the pooled sample for each peak was converted to the percent of parent in the pooled samples:

% of parent in the pooled samples=(total radioactivity of the peak/total radioactivity of the parent peak)×100

The limit of quantification for a radioactivity detector was defined as the ratio of signal to noise (3 to 1) on the radio-chromatogram. The low limits of quantification were 10 and 500 dpm for the TopCount and 13-RAM radio flow-through detector, respectively.

Results and Discussion

Radioactive Recovery

The initial extraction recovery was determined using plasma samples from a subject at 4 hours and 72 hours post-dose with three volumes of MeOH:ACN (20:80) extracting three times. The mean extraction recoveries of radioactivity from 4 and 72 hour samples were 98.43% and 94.99%, respectively. After drying down and reconstitution into MeOH:ACN solution, the reconstitution recoveries were 92.73% and 85.90%, respectively. The overall recoveries were 91.27% and 81.60%, respectively.

Urine centrifugation recoveries determined using 0-8, 24-48, 72-96, and 120-144 hour post-dose samples from the subject ranged between 102% and 104%. Urine reconstitution recovery after lyophilization was 94.7% using pooled samples from a subject.

For pooled fecal samples from 0-48 hours post dose, the extraction, reconstitution, and overall recoveries were 98.48%, 88.80%, and 87.37%, respectively. For pooled fecal samples of 120-168 hours post dose, the extraction, reconstitution, and overall recoveries were 85.85%, 87.69%, and 75.24%, respectively.

The radioactivity recovery from HPLC column for urine sample was 97.05%.

No correction factor was applied to the plasma, urine, and fecal radio-quantitation to account for the recovery.

Metabolite Profiling

In a subject, cabozantinib, compound 9 (cabozantinib sulfate), and compound 19 (cabozantinib N-oxide) were the major peaks on the radio-chromatograms. Compound 2 (demethylated and sulfated fluoroaniline cleavage product) was the major metabolite in plasma samples after 72 hours post-dose. Metabolite compound 7 (fluoroaniline cleavage product) accounted for one of the minor peaks. Metabolite compounds 7, 3 (demethyl cabozantinib glucuronide B), 9, and 10 (methyl ester of fluoroaniline cleavage product) co-eluted using HPLC Method 1.

Representative human urine metabolite profiles, the radio-chromatograms (using HPLC Method 1) of human urine samples from 0-72 hours, 144-192 hours, and 288-336 hours post-dose were collected from a subject. Metabolite compound 6 was the major metabolite in 0-72 hours, 144-192 hours, and 288-336 hours post dose pooled urine samples. In addition to compound 6, metabolite compounds 1, 4, 5, 7, and 19 were observed in the pooled sample of 0-72 hours post dose. Metabolite compounds 1, 4, 5, and 7 were observed in the pooled sample of 144-192 hours post dose. Metabolite compounds 1 and 5 were detected in the pooled sample of 288-336 hours post dose. Parent compound cabozantinib was not observed in urine samples.

Representative human fecal metabolite profiles, the radio-chromatograms (using HPLC Method 1) of human fecal samples from 0-72 hours, 144-192 hours, and 288-336 hours post-dose from a. Parent cabozantinib and metabolites compound 4, 7, 11, and 15 (including compound 16) were observed in the pooled sample of 0-72 hours post dose. Metabolite compounds 4, 7, 11, 15, 16, and 18 were observed in the pooled sample of 144-192 hours post dose. Metabolite compounds 4 and 11 were observed in the pooled sample of 288-336 hours post dose.

Metabolite Identification Using HPLC/MS Analysis

HPLC/MS analysis of authentic standards using HPLC Method 1 showed that the retention times of cabozantinib, fluoroaniline cleavage product (compound 7), sulfate (compound 9), and N-oxide (compound 19) were 20.3, 14.4, 16.5, and 23.1 minutes, respectively.

Plasma, urine, and fecal samples were next analyzed by HOPLC/MS, and the compounds were identified based on their protonated molecular ions and fragmentation patterns.

Metabolite Identification of Cabozantinib and its Metabolites in Human Plasma

The mass spectrum of the peak at approximately 19.1 minutes in the XIC showed the protonated molecular ions at m/z 502. Its product ion spectra showed major fragments at m/z 391, 323, and 297, which is consistent with those of cabozantinib standard. The MS data is summarized in Table 1 and 2.

TABLE 1

HPLC Radiochromatogram Retention Times of Metabolites in Samples from Single Oral Dose of [$^{14}$C] Cabozantinib

| Compound | HPLC Method | Retention Time (min) |
|---|---|---|
| Standards | | |
| 7 | 1 | 14.13 |
| 9 | 1 | 16.45 |
| I | 1 | 20.26 |
| 19 | 1 | 23.06 |
| Plasma | | |
| 1 | 1 | 4.13 |
| 2a/2b | 1 | 9.33 |
| 4 | 1 | 11.87 |
| 5 | 1 | 12.80 |
| 6 | 1 | 13.47 |
| 7 | 1 | 14.13 |
| 9 | 1 | 14.67 |
| I | 1 | 18.67 |
| 19 | 1 | 23.47 |
| Urine | | |
| 1 | 1 | 4.13 |
| 4 | 1 | 11.87 |
| 5 | 1 | 12.80 |
| 6 | 1 | 13.47 |
| 7 | 1 | 14.13 |
| 19 | 1 | 23.47 |
| Feces | | |
| 4 | 1 | 12.67 |
| 7 | 1 | 13.47 |
| 11 | 1 | 16.07 |
| 15 | 1 | 17.87 |
| I | 1 | 19.60 |
| 18 | 1 | 21.03 |
| Hamilton Pooled Sample | | |
| Plasma | | |
| 9 | 3 | 17.36 |
| 7 | 3 | 19.32 |
| 8 | 3 | 19.32 (shoulder) |
| 19 | 3 | 25.20 |
| I | 3 | 37.52 |

TABLE 2

MS Data for Metabolites Using HPLC

| Compound | HPLC Method | HPLC Retention Time | MS (m/z) |
|---|---|---|---|
| I | 1 | 19.10 | 502 |
| 19 | 1 | 21.85 | 518 |
| 9 | 1 | 15.29 | 518 (loss of SO$_3$ from m/z molecular ion m/z at 598) |
| 7 | 1 | 13.36 | 409 |
| 2a | 1 | 10.70 (2a) | 473, 395 (loss of SO$_3$ from m/z molecular ion m/z at 473) |
| 3 | 2 | 15.87 | 488 |
| 8 | 2 | 19.43 | 488 |
| 10 | 2 | 33.56 | 423 |
| 5 | 1 | 13.00 | 489 |
| 6 | 1 | 13.39 | 393 |
| 15 | 1 | 17.60 | 488 |
| 16 | 1 | 17.60 | 518 |
| 13 | 1 | 16.45 | 518 |
| 12 | 1 | 16.45 | 518 |
| 17 | 1 | 18.43 | 518 |

Kinase Activity of Cabozantinib Metabolites

Kinase Dilution

Kinase Activity was measured and profiled by EMD Millipore according to the Kinase Profiler Service Assay Protocols Protocol Guide Volume 57. The results are summarized below in Table 3. Inhibition is indicated as $IC_{50}$ with the following key: $A=IC_{50}$ less than 50 nM, $B=IC_{50}$ greater than 50 nM, but less than 500 nM, $C=IC_{50}$ greater than 500 nM, but less than 5000 nM, and $D=IC_{50}$ greater than 5,000 nM. Depending upon the functionality about the quinazoline or quinoline, exemplary compounds of the invention exhibit selectivity for any of c-Met, KDR, c-Kit, flt-3, and flt-4. Abbreviations for enzymes listed in Table 3 are defined as follows: c-Met refers to hepatocyte growth factor receptor kinase; RET refers to RET proto-oncogene kinase; KDR refers to kinase insert domain receptor tyrosine kinase; flt-1 alpha, flt-3, and flt-4, fms-like tyrosine kinases, representative of the FLK family of receptor tyrosine kinases; and Aurora B MP refers to Aurora B kinase. When a percentage is listed instead of an $IC_{50}$ value, it indicates percent inhibition at 1 uM. Empty cells in the tables indicate lack of data only.

TABLE 3

Kinase Activity

| Compound ID | MOLSTRUCTURE | c-Met Std (IC50) (nM) | RET Std (IC50) (nM) | KDR Std (IC50) (nM) | Flt-1 Alpha (IC50) (nM) | Flt-3 Std (IC50) (nM) | Flt-4 Std (IC50) (nM) | Aurora B MP 8pt Std (IC50) (nM) |
|---|---|---|---|---|---|---|---|---|
| Cabozantinib | 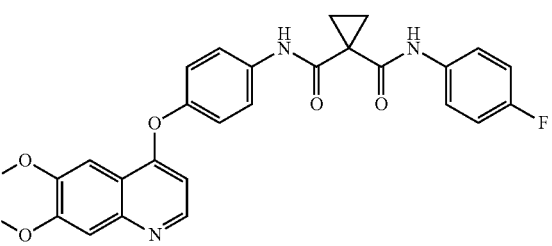 | A | A | A | A | A | A | |
| 16 | 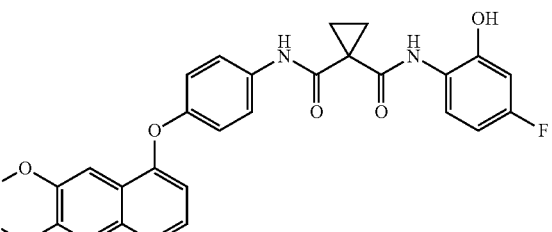 | A | | A | C | A | | B |
| 13 | 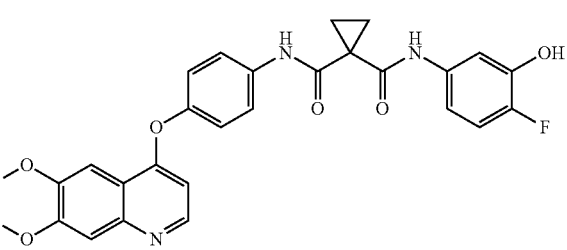 | A | | A | C | A | | B |
| 2a | 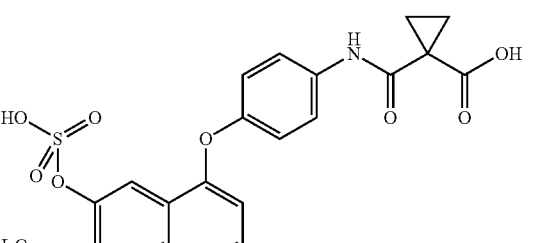 | ≥50% @ 1 µM | ≤25% @ 1 µM | ≤25% @ 1 µM | ≤25% @ 1 µM | ≤25% @ 1 µM | ≥25% @ 1 µM | ≤25% @ 1 µM |

TABLE 3-continued

Kinase Activity

| Compound ID | MOLSTRUCTURE | c-Met Std (IC50) (nM) | RET Std (IC50) (nM) | KDR Std (IC50) (nM) | Flt-1 Alpha (IC50) (nM) | Flt-3 Std (IC50) (nM) | Flt-4 Std (IC50) (nM) | Aurora B MP 8pt Std (IC50) (nM) |
|---|---|---|---|---|---|---|---|---|
| 2b | | | | | | | | |
| 9 | | ≥75% @ 1 μM | ≥75% @ 1 μM | ≤25% @ 1 μM | ≥50% @ 1 μM | ≥50% @ 1 μM | ≥75% @ 1 μM | ≥75% @ 1 μM |
| 19 | | B | | B | | C | | C |
| 7 | | D | | D | | C | | C |

Metabolite Synthesis and Structural Data

6-Desmethyl Acid

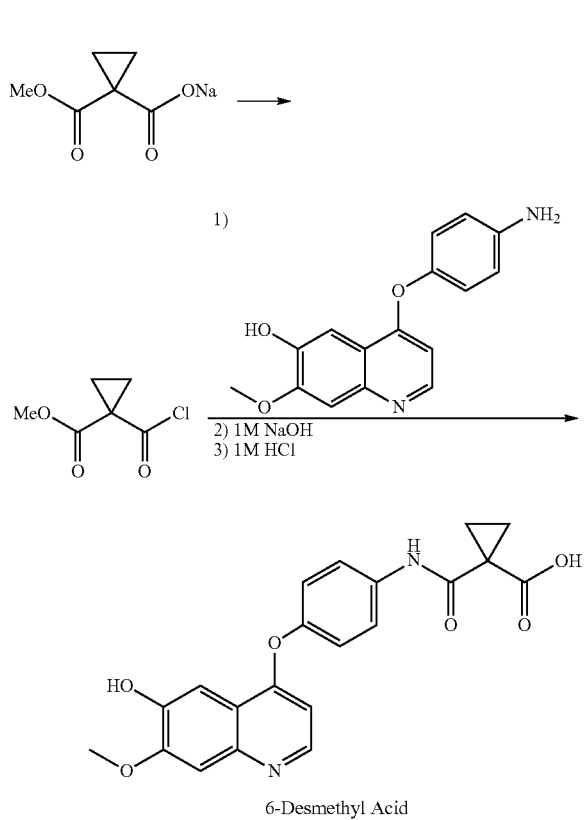

6-Desmethyl Acid

In a vessel, 4-(4-aminophenoxy)-7-methoxyquinolin-6-ol (15.0 g; 53.3 mmol), which was prepared according to Scheme 4, and potassium carbonate (29.5 g; 213.3 mmol; 4 equiv) were suspended in THF (210 mL; 14 vol) and water (90 mL; 6 vol) at 20° C. In a separate vessel, sodium 1-(methoxycarbonyl)cyclopropanecarboxylate (17.71 g; 106.6 mmol; 2 equiv.) was suspended in THF (90 mL; 6 vol). DMF (120 µL; 3 mol %) was added and cooled to less than 15° C. Oxalyl chloride (9.34 mL; 106.6 mmol; 2 equiv.) was added over 90 minutes, and the reaction was aged 2 hours at 10-15° C. The acid chloride slurry was added to the cabozantinib suspension over 2 hours at 20-25° C. and aged at least 3 hours, whereupon HPLC analysis showed greater than 99% conversion to a mixture of the mono- and biscarbonylated material. The reaction mixture was filtered over Celite®, washed with THF (30 mL; 2 vol), and the layers were separated. 1 M NaOH (150 mL; 10 vol) was added to the upper THF layer, and the mixture was heated at 40° C. for 1 hour whereupon HPLC analysis showed greater than 99% saponified product. The mixture was cooled to 25° C., and the upper THF layer was removed. The aqueous layer was acidified to pH 3-4 with 1 M HCl to precipitate the product and was aged for 1 hour. The precipitate was filtered, washed with water (90 mL, 6 vol), and dried under vacuum (greater than 20 psig) with nitrogen bleed at 50° C. to give a grey to brown powder. $^1$H-NMR (DMSO-$d_6$, 400 MHz) δ 10.8-11.0 (br s, 1H), 10.7 (s, 1H), 8.65 (d, J=6.9 Hz, 1H), 7.81 (d, J=9.3 Hz, 2H), 7.67 (s, 1H), 7.58 (s, 1H), 7.32 (d, J=9.3 Hz, 2H), 6.69 (d, J=6.9 Hz, 1H), 4.01 (s, 3H), 2.48-2.53 (m, 4H). MS (ESI-) m/z 393 [M−H]$^−$.

6-Hydrogen Sulfate 6-Desmethyl Acid

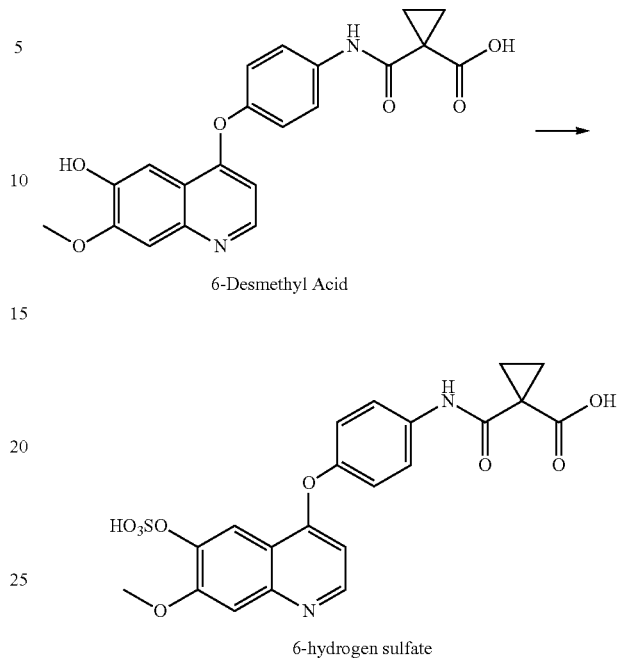

6-Desmethyl Acid 6-hydrogen sulfate

6-Desmethyl acid (120 mg; 0.30 mmol), potassium hydroxide (118 mg; 2.1 mmol; 7 equiv.), and sulfur trioxide trimethyl amine complex (292 mg; 2.1 mmol; 7 equiv.) was dissolved in water (3 mL; 25 vol) and heated to 70° C. for 2 hours whereupon analysis by HPLC showed greater than 99% conversion. The reaction mixture was then cooled in an ice bath and acidified dropwise with 1 N aq. H$_2$SO$_4$ to approximately pH 1. The slurry was aged at 25° C. for 1 hour, filtered, washed with water (3 mL; 25 vol), and deliquored. The wet cake was then washed with acetone (3 mL; 25 vol) and dried at 35° C. under vacuum (greater than 20 psig) with nitrogen bleed for 24 hours to give a beige powder.

Alternatively, 6-desmethyl acid (120 mg; 0.30 mmol) was suspended in MeCN (50 vol, 6 mL), and triethylamine (1.27 mL, 9.12 mmol, 30 equiv.) was added and then cooled in an ice bath. Chlorosulfonic acid (101 µL, 1.52 mmol, 5 equiv.) was added dropwise, and the reaction was then heated to 70° C. for 1 hour whereupon analysis by HPLC showed greater than 98 percent conversion. The reaction mixture was then cooled in an ice bath for 2 hours in which a precipitate was formed. The precipitate was removed with filtration, rinsing with cold MeCN (50 vol). The MeCN solution was then concentrated to approximately 20 vol (approximately 2 mL) and quenched with 100 vol 1N HCl and cooled in an ice bath to give a fine precipitate that was filtered, washed with 50 vol water and 50 vol acetone, and dried at 35° C. under vacuum (greater than 20 psig) with nitrogen bleed for 24 hours to give a beige powder. $^1$H-NMR (DMSO-$d_6$, 400 MHz) δ 10.8 (s, 1H), 8.83 (d, J=5.9 Hz, 1H), 8.5 (s, 1H), 7.85 (d, J=8.5 Hz, 2H), 7.52 (s, 1H), 7.40 (d, J=8.5 Hz, 2H), 6.84 (d, J=5.9 Hz, 1H), 4.04 (s, 3H), 3.20-3.70 (br s, 1H), 1.39-1.48 (br s, 4H). MS (ESI-) m/z 473 [M−H]$^−$, 236.

Ortho-Hydroxy-Cabozantinib

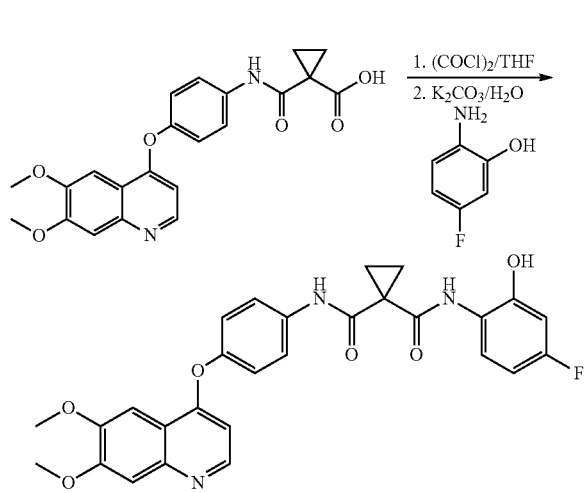

A flask was charged with the carboxylic acid (0.84 g; 2.1 mmol), THF (1.2 mL), and DMF (5 µL), and cooled to 15° C. To this slurry was added oxalyl chloride (0.17 mL; 2.1 mmol) dropwise over approximately 20 minutes. After 2 hours, the acid chloride slurry was added to another vessel containing a stirred suspension of the aniline (0.2 g, 1.6 mmol), potassium carbonate (0.63 g, 4.6 mmol) in THF (2.8 mL), and water (1 mL) over approximately 15 minutes. After 3 hours, HPLC analysis showed complete conversion to the product. Stirring was stopped, the lower aqueous layer was removed, and water (30 mL) was added to precipitate the product. The product was then collected by filtration and washed with 1:1 THF-water solution (2×10 mL) to afford a pale grey solid. It was then further purified by flash chromatography on silica gel using methanol/dichloromethane as the mobile phase.

Alternatively, a suspension of the carboxylic acid (4.08 g; 10 mmol), aniline (1.52 g; 12 mmol), and triethylamine (2.7 mL; 20 mmol) in acetonitrile (100 mL) was treated with EDAC (2.30 g; 12 mmol) and HOBt (0.5 g; 3 mmol). The slurry was stirred overnight at room temperature, and the reaction progress was monitored by HPLC. At the end of the reaction, 150 mL of water was added, and the precipitated product was collected by filtration, washed with water, and then purified by flash chromatography. $^1$H-NMR (DMSO-$d_6$, 400 MHz) δ 10.46 (br s, 1H), 10.29 (br s, 1H), 10.0 (br s, 1H), 8.47 (d, 1H), 7.92 (dd, 1H), 7.73 (dd, 2H), 7.51 (s, 1H), 7.40 (s, 1H), 7.28 (dd, 2H), 6.68 (dd, 1H), 6.62 (dt, 1H), 6.45 (d, 1H), 3.95 (s, 3H), 3.94 (s, 3H), 1.60-1.55 (m, 4H). $^{13}$C NMR (DMSO-$d_6$, 100 MHz) δ 169.82, 167.67, 159.91, 157.51, 152.58, 149.97, 149.35, 149.09, 148.98, 148.86, 146.49, 135.72, 123.00, 122.97, 122.91, 122.43, 121.30, 115.17, 107.86, 105.10, 104.87, 103.16, 102.43, 102.19, 99.08, 55.74, 55.71, 55.66, 30.02, 16.51.

MS (APCI+) m/z 518.3 [M+H]$^+$, 500.3.

Cabozantinib-Hydroxysulfate

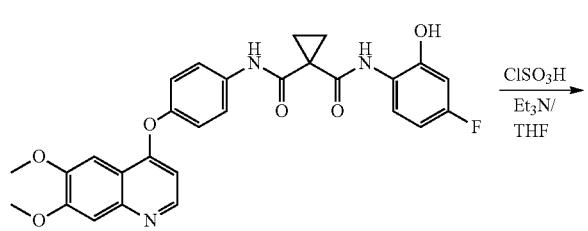

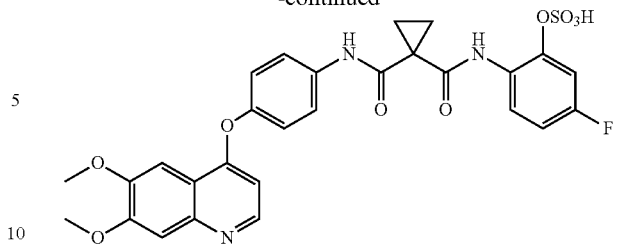

A suspension of the hydroxy-cabozantinib (0.95 g; 1.9 mmol) in THF (20 mL) was added triethylamine (5 mL; 36 mmol), and cooled to below 5° C. Chlorosulfonic acid (1 mL; 15 mmol) was added dropwise such that the temperature remained below 10° C., over approximately 15 minutes. After stirring overnight at room temperature, HPLC analysis showed approximately 5 percent of starting material remaining. The reaction mixture was treated with aqueous 1 N HCl (25 mL). The precipitated product was collected by filtration, washed with water (4×25 mL), and dried under vacuum to yield an off-white solid (937 mg; 82 percent crude yield). Analysis by AN-HPLC showed that the product was 90.8% pure, the major impurity being the starting material. The product was purified to greater than 99 percent (AN-HPLC) by preparative HPLC on a C18 column, using aqueous ammonium acetate/acetonitrile mobile phase system. $^1$H-NMR (DMSO-$d_6$, 400 MHz) δ 10.39 (s, 1H), 9.69 (s, 1H), 8.81 (d, 1H), 7.95 (dd, 1H), 7.85 (d, 1H), 7.77 (s, 1H), 7.51 (s, 1H), 7.11 (s, 1H), 7.08 (dd, 1H), 6.93 (dd, 1H), 6.45 (d, 1H), 4.05 (s, 3H), 4.04 (s, 3H), 1.53 (s, 4H). MS (ESI-) m/z 596.0 [M−H]$^−$.

Meta-Hydroxy-Cabozantinib

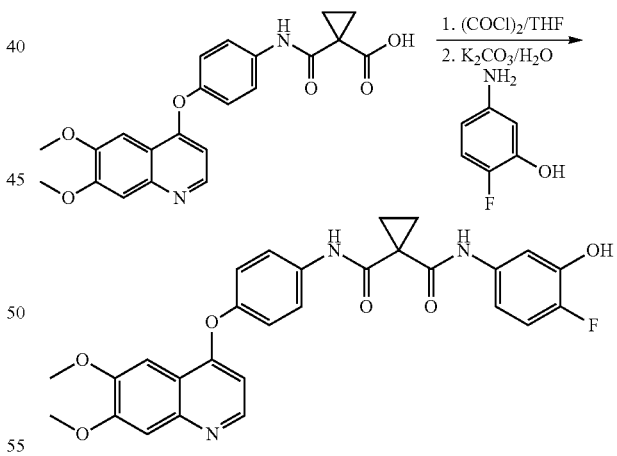

A flask was charged with the carboxylic acid (0.84 g; 2.1 mmol), THF (1.2 mL), and DMF (5 µL), and cooled to 15° C. To this slurry was added oxalyl chloride (0.17 mL; 2.1 mmol) dropwise over approximately 20 minutes. After 2 hours, the acid chloride slurry was added to another vessel containing a stirred suspension of the aniline (0.2 g, 1.6 mmol), potassium carbonate (0.63 g, 4.6 mmol) in THF (2.8 mL), and water (1 mL) over approximately 15 minutes. After 90 minutes, HPLC analysis showed complete conversion to the product. Stirring was stopped, and the lower aqueous layer was removed and extracted with ethyl acetate (15 mL). The organic layers were combined, dried over anhydrous MgSO$_4$, filtered, and concentrated to yield a brown solid. The solid was then further purified by flash chromatography on silica gel using ethyl acetate/heptane as the mobile phase. $^1$H-NMR (DMSO-d$_6$, 400 MHz) δ 10.15 (br s, 1H), 9.96 (br s, 1H), 9.89 (br s, 1H), 8.46 (d, 1H), 7.76 (d, 1H), 7.50 (s, 1H), 7.41 (d, 2H), 7.39 (s, 1H), 7.22 (d, 2H), 7.07-6.98 (m, 2H), 6.42 (d, 1H), 3.94 (s, 3H), 3.93 (s, 3H), 1.46 (br s, 4H). $^{13}$C NMR (DMSO-d$_6$, 100 MHz) δ 168.27, 167.95, 160.02, 152.56, 149.48, 149.33, 148.86, 148.56, 146.46, 146.21, 144.52, 144.39, 136.45, 135.33, 135.31, 122.23, 121.22, 115.63, 115.44, 115.15, 111.29, 111.23, 110.26, 107.85, 103.04, 99.08, 55.73, 55.71, 31.66, 15.40. MS (APCI+) m/z 518.3 [M+H]$^+$, 502.3.

Cabozantinib N-Oxide

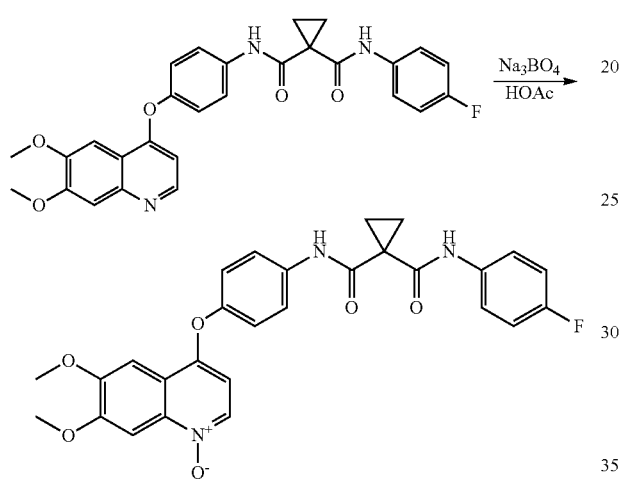

A flask was charged with cabozantinib (3.21 g; 6.4 mmol), acetic acid (32.1 mL), and sodium perborate tetrahydrate (1.98 g, 12.8 mmol) and heated to 65° C. and stirred overnight. After 24 hours, HPLC analysis showed about 38:62 starting material: product. More oxidant (1.98 g; 12.8 mmol) was added, and heating continued overnight. Solvents were removed under vacuum, and the residue was purified by flash chromatography using dichloromethane-methanol gradient (dichloromethane to 10% methanol-dichloromethane) to obtain 0.95 g of the product as a white solid. $^1$H-NMR (DMSO-d$_6$, 400 MHz) δ 10.20 (br s, 1H), 10.08 (br s, 1H), 8.28 (d, 1H), 7.90 (s, 1H), 7.74 (d, 2H), 7.64 (dd, 2H), 7.48 (s, 1H), 7.23 (d, 2H), 7.15 (t, 2H), 6.45 (d, 1H), 3.97 (s, 3H), 3.94 (s, 3H), 1.47 (br s, 4H). $^{13}$C NMR (DMSO-d$_6$, 100 MHz) δ 172.11, 168.18, 168.13, 159.49, 157.09, 153.34, 150.72, 150.57, 149.98, 137.41, 136.32, 135.24, 135.21, 134.06, 122.44, 122.36, 122.19, 120.65, 117.23, 11.17, 114.95, 104.37, 100.34, 99.12, 56.09, 56.03, 31.59, 15.42. MS (APCI+) m/z 518.3 [M+H]$^+$.

1-[4-(6,7-Dimethoxy-quinolin-4-yloxy)-phenylcarbamoyl]-cyclopropane carboxylic acid

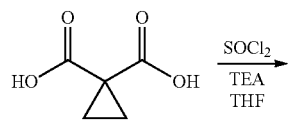

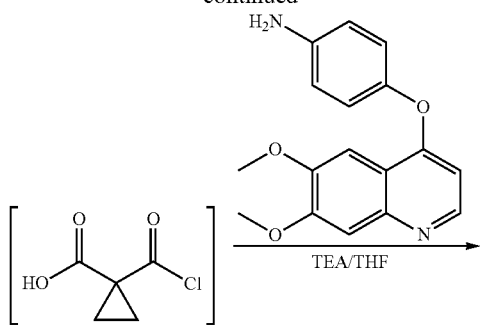

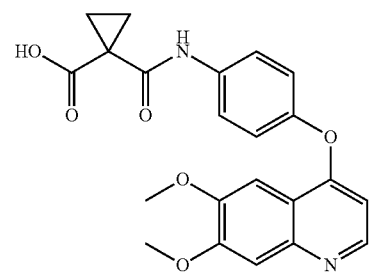

To the cyclopropyl di-carboxylic acid (449 mg, 3.45 mmol) in THF (3.5 mL) was added TEA (485 μL, 3.45 mmol). The resulting solution was stirred at room temperature under a nitrogen atmosphere for 40 minutes before adding thionyl chloride (250 μL, 3.44 mmol). The reaction was monitored by LCMS for the formation of mono acid chloride (quenched the sample with MeOH and looked for corresponding mono methyl ester). After 3 hours stirring at room temperature, 4-(6,7-dimethoxy-quinolin-4-yloxy)-phenylamine (1.02 g, 3.44 mmol) was added as a solid, followed by more THF (1.5 mL). The reaction continued to stir at room temperature for 16 hours. The resulting thick slurry was diluted with EtOAc (10 mL) and extracted with 1N NaOH. The biphasic slurry was filtered, and the aqueous phase was acidified with concentrated HCl to pH or approximately 6 and filtered. Both solids were combined and washed with EtOAc, then dried under vacuum. The desired product, 1-[4-(6,7-dimethoxy-quinolin-4-yloxy)-phenylcarbamoyl]-cyclopropanecarboxylic acid, was obtained (962 mg, 68.7 percent yield, 97 percent pure) as a white solid. $^1$H NMR (D$_2$O/NaOH): 7.97 (d, 1H), 7.18 (d, 2H), 6.76 (m, 4H), 6.08 (d, 1H), 3.73 (s, 3H), 3.56 (s, 3H), 1.15 (d, 4H).

The foregoing disclosure has been described in some detail by way of illustration and example for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:
1. A pharmaceutical composition comprising a compound selected from the group consisting of:
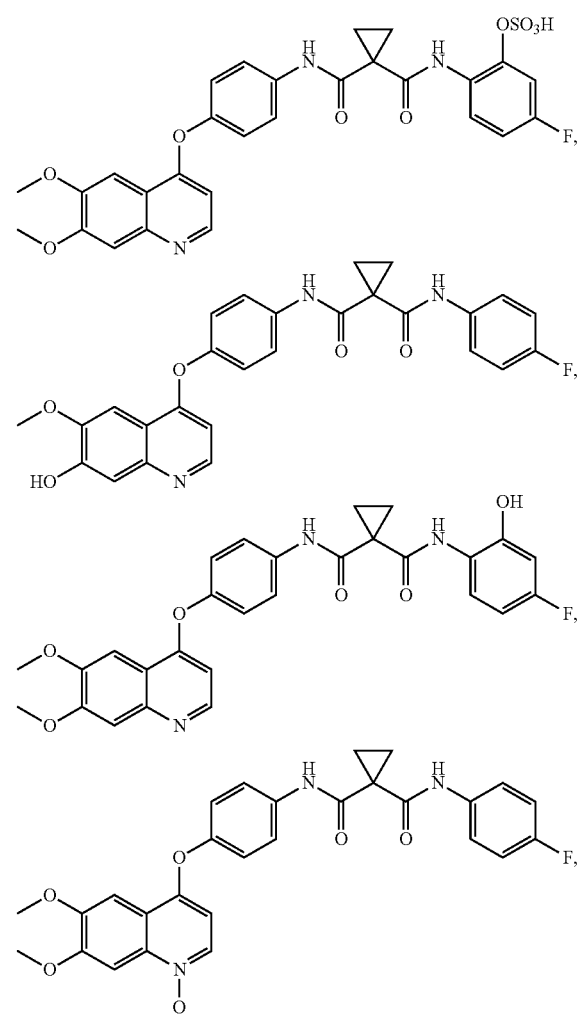
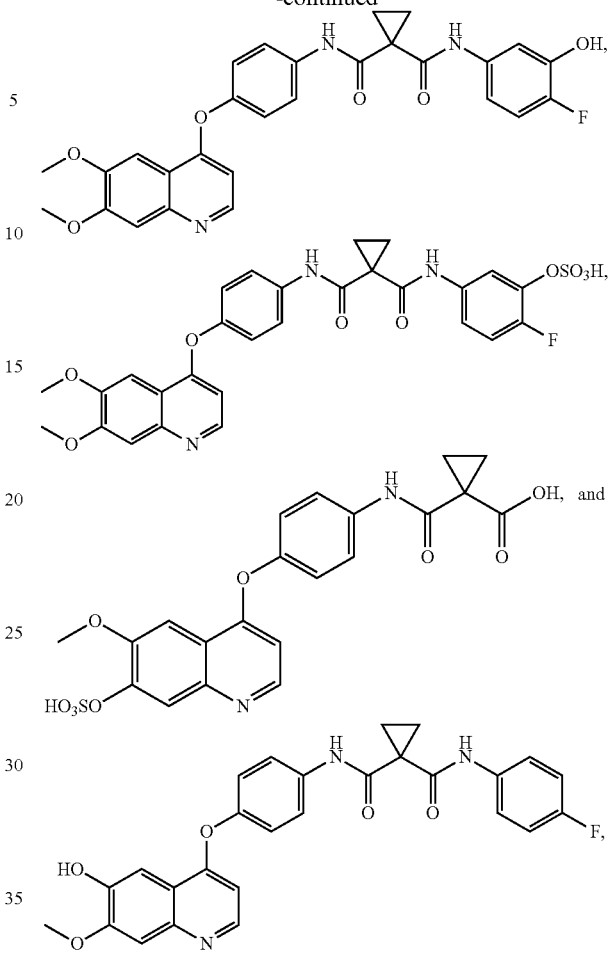
or a pharmaceutically acceptable salt thereof; and at least one pharmaceutically acceptable carrier.
2. The composition of claim 1, which is suitable for oral administration.
* * * * *